(12) United States Patent
Nesvadba et al.

(10) Patent No.: US 11,021,560 B2
(45) Date of Patent: Jun. 1, 2021

(54) CATALYST FOR THE PREPARATION OF POLYURETHANES

(71) Applicant: BASF SE, Ludwigshafen am Rhein (DE)

(72) Inventors: Peter Nesvadba, Basel (CH); Julio Albuerne, Lemförde (DE); Lucienne Bugnon Folger, Basel (CH); Frederique Wendeborn, Basel (CH)

(73) Assignee: BASF SE, Ludwigshafen am Rhein (DE)

(*) Notice: Subject to any disclaimer, the term of this patent is extended or adjusted under 35 U.S.C. 154(b) by 244 days.

(21) Appl. No.: 15/777,272

(22) PCT Filed: Nov. 18, 2016

(86) PCT No.: PCT/EP2016/078135
§ 371 (c)(1),
(2) Date: May 18, 2018

(87) PCT Pub. No.: WO2017/085252
PCT Pub. Date: May 26, 2017

(65) Prior Publication Data
US 2018/0327534 A1    Nov. 15, 2018
US 2020/0172652 A9    Jun. 4, 2020

(30) Foreign Application Priority Data

Nov. 19, 2015   (EP) .................................... 15195384

(51) Int. Cl.
| | |
|---|---|
| *C08G 18/18* | (2006.01) |
| *C07C 235/84* | (2006.01) |
| *C07C 311/21* | (2006.01) |
| *C07C 229/08* | (2006.01) |
| *C07C 235/74* | (2006.01) |
| *C07C 235/76* | (2006.01) |
| *C08G 18/48* | (2006.01) |
| *C08G 18/76* | (2006.01) |
| *C08G 18/20* | (2006.01) |
| *C07D 471/08* | (2006.01) |
| *C07D 471/04* | (2006.01) |

(52) U.S. Cl.
CPC ........ *C08G 18/1875* (2013.01); *C07C 229/08* (2013.01); *C07C 235/74* (2013.01); *C07C 235/76* (2013.01); *C07C 235/84* (2013.01); *C07C 311/21* (2013.01); *C07D 471/04* (2013.01); *C07D 471/08* (2013.01); *C08G 18/1825* (2013.01); *C08G 18/1841* (2013.01); *C08G 18/2063* (2013.01); *C08G 18/4812* (2013.01); *C08G 18/4825* (2013.01); *C08G 18/4829* (2013.01); *C08G 18/7621* (2013.01); *C08G 18/7664* (2013.01); *C08G 18/7671* (2013.01)

(58) Field of Classification Search
None
See application file for complete search history.

(56) References Cited

U.S. PATENT DOCUMENTS

| | | | | |
|---|---|---|---|---|
| 4,146,509 | A | * | 3/1979 | Markusch .......... C08G 18/3895 521/115 |
| 4,540,781 | A | * | 9/1985 | Barsa .................. C08G 18/022 544/193 |
| 4,582,861 | A |   | 4/1986 | Galla et al. |
| 5,212,306 | A |   | 5/1993 | Savoca et al. |
| 6,432,864 | B1 |   | 8/2002 | Wendel et al. |
| 2017/0015762 | A1 |   | 1/2017 | Debling et al. |
| 2017/0190080 | A1 |   | 7/2017 | Rischko et al. |
| 2017/0198086 | A1 |   | 7/2017 | Alburene et al. |
| 2018/0016199 | A1 |   | 1/2018 | Nave et al. |
| 2018/0086872 | A1 |   | 3/2018 | Otero Martinez et al. |
| 2018/0134633 | A1 |   | 5/2018 | Nave et al. |
| 2018/0148551 | A1 |   | 5/2018 | Goeschel et al. |
| 2018/0186923 | A1 |   | 7/2018 | Otero Martinez et al. |

FOREIGN PATENT DOCUMENTS

| | | | |
|---|---|---|---|
| EP | 0989146 A1 | 3/2000 | |
| EP | 2050775 A1 | 4/2009 | |
| GB | 1182014 A * | 2/1970 | ......... C08G 18/2063 |
| JP | 2014055114 A * | 3/2014 | .......... C07C 233/65 |
| WO | 9101970 A2 | 2/1991 | |
| WO | 2011094244 A1 | 8/2011 | |
| WO | 2013097928 A1 | 7/2013 | |
| WO | 2015150508 A1 | 10/2015 | |
| WO | 2016034963 A1 | 3/2016 | |
| WO | 2016097318 A1 | 6/2016 | |

OTHER PUBLICATIONS

Machine translation of JP-2014055114-A (no date).*
M Kempf et al., "Effect of impact damage on the compression performance of glass and carbon fibre reinforced composits", 18th International Conference on Composite Materials, published 2011—iccm-central.org. 6 pages.
Kunststoffhandbuch, vol. 7, Polyurethane, Carl Hanser Verlag, 3rd edition 1993, section 3.1. 19 pages. No translation available.
Kunststoffhandbuch, vol. VII, edited by Vieweg and Höchtlen, Carl Hanser Verlag, Munich 1966 (pp. 103-113). No translation available.
Jha, Amitabh; Chou, Ting-Yi; Al Jaroudi, Zainab; Ellis, Bobby D.; Cameron, T. Stanley, Beilstein Journal of Organic Chemistry, 2014, 10, 848-857.

* cited by examiner

*Primary Examiner* — Michael J Feely
(74) *Attorney, Agent, or Firm* — Armstrong Teasdale LLP

(57) ABSTRACT

Novel thermolatent bases and their use as catalysts for the preparation of polyurethanes or epoxy resins are disclosed herein. A process for the preparation of polyurethanes or epoxy resins in the presence of the catalyst is also disclosed.

7 Claims, 1 Drawing Sheet

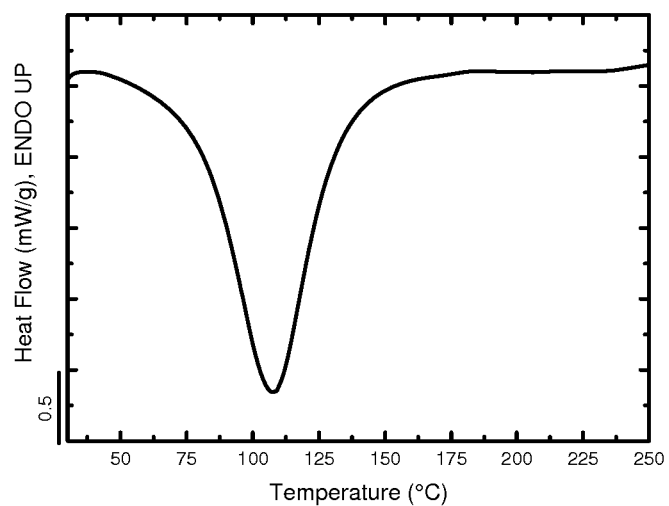

CATALYST FOR THE PREPARATION OF POLYURETHANES

CROSS-REFERENCE TO RELATED APPLICATIONS

This application is a U.S. National Phase Application of PCT/EP2016/078135, filed Nov. 18, 2016, which claims the benefit of priority to EP Application No. 15195384.1, filed Nov. 19, 2015, the contents of which are hereby expressly incorporated by reference in their entirety.

Object of the invention are novel thermolatent bases and their use as catalysts for the preparation of polyurethanes as well as a process for the preparation of polyurethanes in the presence of the catalyst according to the present invention.

Cellular or compact polyurethanes, in particular polyurethane casting elastomers and thermoplastic polyurethanes (TPU), have long been known from numerous patent and literature publications. Their industrial importance is based on the combination of valuable mechanical properties with the advantages of low-cost processing methods. The use of different chemical formative components in different ratios makes it possible to prepare thermoplastically processable or crosslinked, compact or cellular polyurethanes having a wide variety of mechanical and processing properties. An overview of polyurethanes and their properties and applications is given, for example, in Kunststoff-Handbuch, Volume 7, Polyurethane, 1st Edition, 1966, edited by Dr. R. Vieweg and Dr. A. Hochtlen, and 2nd Edition, 1983, and also 3rd Edition, 1993, edited by Dr. G. Oertel, (Carl Hanser Verlag, Munich, Vienna).

Polyurethanes are produced industrially in a reaction of a polyisocyanate with polyol or polyamine compounds. The reactions are almost always catalyzed to provide cure times that are short enough for the manufacturing process to be economically feasible.

Some manufacturing processes require a delayed cure. For example, some manufacturing processes require that a polyurethane-forming mixture to be prepared and then applied to some other material or mold before it is cured. Some "working time", which may be up to several minutes in some processes, may be needed to apply the mixture and to manipulate it further, before the mixture builds a high molecular weight and becomes too viscous to work with. In all of these processes, some delay in the initial cure is wanted, to provide enough time that the polyurethane-forming mixture can be applied and manipulated. However, after some predetermined "working time", it is usually desirable that the reaction mixture cures rapidly. The rapid cure allows manufacturing equipment to handle greater volumes of product per unit time and thus allows for increased production rates and lower manufacturing costs.

For example WO 2013/097928 A2 discloses a crosslinking two-component polyurethane composition consisting of a constituent A containing polyols and additives, and a constituent B containing between 100 and 65 wt. % of aromatic polyisocyanates, between 0 and 35 wt. % of aliphatic polyisocyanates, and between 0.05 and 3.0 wt. % of a retarder, and optionally additives, the mixed composition having a pot life of longer than 60 minutes. The two-component polyurethane composition is suitable as an adhesive and as a matrix substance for composite materials. Also M Kempf et al., "Effect of impact damage on the compression performance of glass and carbon fibre reinforced composits", 18$^{th}$ International Conference on Composite Materials, published 2011—iccm-central.org focusses on the properties of fiber reinforced polyurethane composits.

Previous efforts to provide a delayed cure have focused on the selection of the catalyst. Various types of delayed action catalysts are known. Some are simply relatively inactive catalysts, and the delayed action is mainly an artifact of a generally slow cure. These catalysts can provide for good working time, but the slow cure means that line processing speeds are slow and/or in-mold residence times are long, and for that reason these catalysts are often not useful in commercial processes.

A way to achieve this is to use latent catalysts, which will be inert at a chosen temperature, but become active at a higher temperature. Reference is made for example to WO 2011/094244, EP 989146 A, U.S. Pat. No. 5,212,306, or U.S. Pat. No. 4,582,861.

The literature describes various families of thermolatent bases catalysts for the synthesis of polyurethanes which are inactive at room temperature, but become active at a elevated temperature They can be used for example for mold applications, where the viscosity of the system has to stay low until the mold is filled up, but where the polymerization-crosslinking process must start at a defined higher temperature and be quick in order for processing time to stay as short as possible. The latent catalysts known are either not latent enough and start being active at too low temperatures or are not active enough, i.e. have weak catalytic activity once the activation temperature is reached. There is therefore a need for developing better thermolatent base catalysts showing a sharper activation profile.

This problem is solved according to the present invention by a compound (C) selected from the group consisting of compounds of the general formula (Ia) or (Ib)

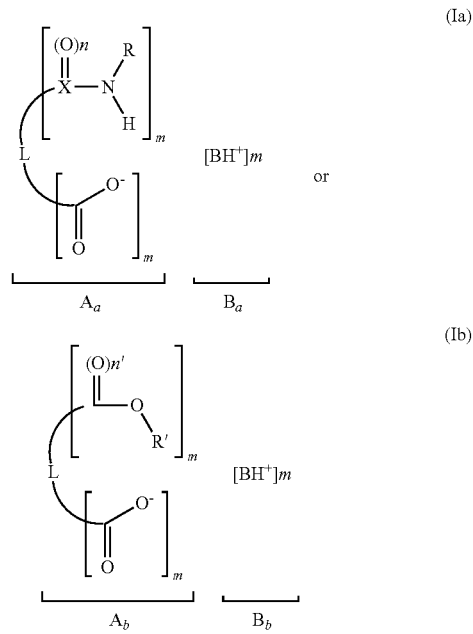

wherein
n is 0 or 1 when X is a carbon atom,
n is 2 when X is a sulfur atom,
n' is 0 or 1, m is an integer from 1 to 6,
R is selected from monovalent, or divalent, or trivalent or polyvalent residues, wherein
  when R is monovalent, R is H, OH, substituted or unsubstituted, linear or branched $C_1$-$C_{18}$ alkyl, $C_5$-$C_7$ cycloalkyl which can be substituted by OH, $OR^1$ or $NR^2R^3$, and which may be interrupted by one or more —O—, —S— or —$NR^4$—;
  when R is divalent, R is substituted or unsubstituted, linear or branched $C_3$-$C_{18}$ alkylene, $C_5$-$C_7$ cycloalkylene which can be substituted by OH, $OR^1$ or $NR^2R^3$, and which may be interrupted by one or more —O—, —S— or —$NR^4$—;
  when R is trivalent, R is selected from $N(CH_2-CH_2-*)_3$,

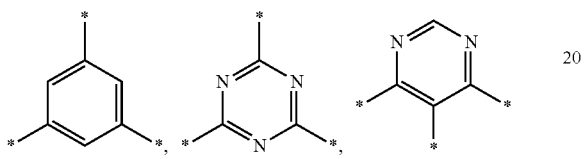

R' is linear or branched $C_1$-$C_5$ alkyl substituted by $NHR^2$,
B is a nitrogen containing organic base,
L is a $C_1$-$C_8$ substituted or unsubstituted alkylene chain, or a substituted or unsubstituted $C_6$ cycloalkylene chain, or substituted or unsubstituted $C_9$-$C_{11}$ polycyclic chain, or a substituted or unsubstituted double bond, which can be interrupted by O, S, $NR^4$, or a substituted or unsubstituted $C_3$ to $C_4$ alkenylene chain, or a substituted or unsubstituted benzene ring, or substituted or unsubstituted naphthalene ring,
$R^1$ is H, $C_1$-$C_{18}$ alkyl,
$R^2$ and $R^3$, independently are hydrogen, unsubstituted or substituted $C_1$-$C_{18}$alkyl or phenyl; or $R^2$ and $R^3$ together with the nitrogen atom to which they are bonded form a 5 or 6 membered-ring which may contain a further heteroatom,
$R^4$ is H, unsubstituted or substituted $C_1$-$C_{18}$alkyl, and
the ratio between $A_a$ and $B_a$ or between $A_b$ and $B_b$ ranges from 0.5:1 to 10:1.

Furthermore, the present invention relates to a process for preparing a polyurethane comprising reacting at least one polyisocyanate with a polyol composition comprising at least one polyol in the presence of a catalyst composition comprising at least one compound (C) selected from the group consisting of compounds of the general formula (Ia) or (Ib)

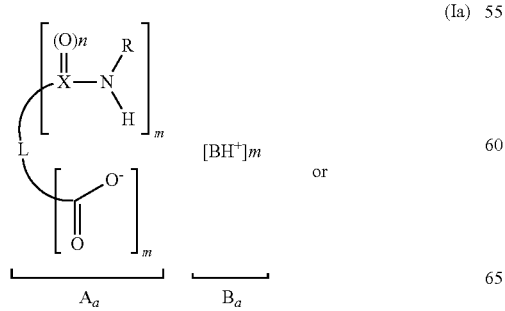

(Ia)

or

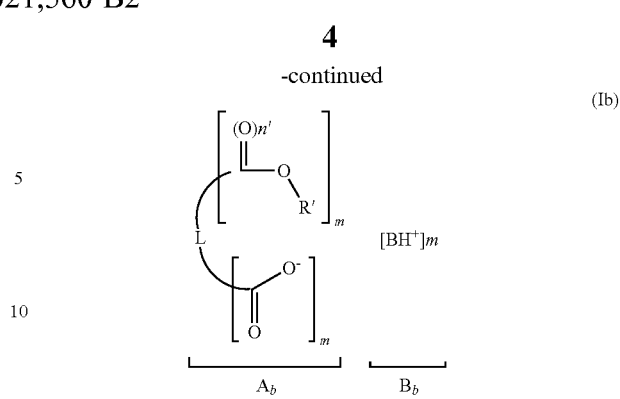

(Ib)

wherein
n is 0 or 1 when X is a carbon atom,
n is 2 when X is a sulfur atom,
n' is 0 or 1,
m is an integer from 1 to 6,
R is selected from monovalent, or divalent, or trivalent or polyvalent residues, wherein
  when R is monovalent, R is H, OH, substituted or unsubstituted, linear or branched $C_1$-$C_{18}$ alkyl, $C_5$-$C_7$ cycloalkyl which can be substituted by OH, $OR^1$ or $NR^2R^3$, and which may be interrupted by one or more —O—, —S— or —$NR^4$—;
  when R is divalent, R is substituted or unsubstituted, linear or branched $C_3$-$C_{18}$ alkylene, $C_5$-$C_7$ cycloalkylene which can be substituted by OH, $OR^1$ or $NR^2R^3$, and which may be interrupted by one or more —O—, —S— or —$NR^4$—;
  when R is trivalent, R is selected from $N(CH_2-CH_2-*)_3$,

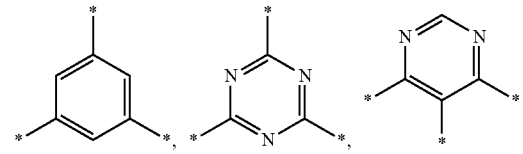

R' is linear or branched $C_1$-$C_5$ alkyl substituted by $NHR^2$,
B is a nitrogen containing organic base,
L is a $C_1$-$C_8$ substituted or unsubstituted alkylene chain, or a substituted or unsubstituted $C_6$ cycloalkylene chain, or substituted or unsubstituted $C_9$-$C_{11}$ polycyclic chain, or a substituted or unsubstituted double bond, which can be interrupted by O, S, $NR^4$, or a substituted or unsubstituted $C_3$ to $C_4$ alkenylene chain, or a substituted or unsubstituted benzene ring, or substituted or unsubstituted naphthalene ring,
$R^1$ is H, $C_1$-$C_{18}$ alkyl,
$R^2$ and $R^3$, independently are hydrogen, unsubstituted or substituted $C_1$-$C_{18}$alkyl or phenyl; or $R^2$ and $R^3$ together with the nitrogen atom to which they are bonded form a 5 or 6 membered-ring which may contain a further heteroatom,
$R^4$ is H, unsubstituted or substituted $C_1$-$C_{18}$alkyl, and
the ratio between $A_a$ and $B_a$ or between $A_b$ and $B_b$ ranges from 0.5:1 to 10:1.

BRIEF DESCRIPTION OF FIGURES

FIG. 1 is a graph depicting an exemplary curing reaction between polyol and isocyanate components in accordance with the present disclosure.

It was surprisingly found that salts of bases with acids which undergo thermally induced cyclization into less or non acidic products according to general formula (Ia) or (Ib) can be used as thermolatent catalyst liberating the base upon heating, i.e. the compound (C) as defined above can be used as thermolatent catalyst.

The compound (C) is selected from the group consisting of compounds of the general formula (Ia) or (Ib). When m is 1, the compound (C) is selected from the group consisting of compounds of the general formula (I'a) or (I'b). When m is 1 and n and n' is 1, the compound (C) is selected from the group consisting of compounds of the general formula (I"a) or (I"b).

According to the present invention, n is 0 or 1 when X is a carbon atom, preferably n is 1 when X is a carbon atom. Generally, n is 2 when X is a sulfur atom.

In formula (Ia) od (Ib) or in formula (I'a) or (I'b), n' is 0 or 1.

According to the present invention, m is an integer from 1 to 6, preferably, m is 1 or 2, more preferable, m is 1.

R is selected from monovalent, or divalent, or trivalent or polyvalent residues. Preferably, R is a monovalent, divalent or trivalent rest, more preferable R is monovalent.

When R is monovalent, R is H, OH, substituted or unsubstituted, linear or branched $C_1$-$C_{18}$ alkyl, $C_5$-$C_7$ cycloalkyl which can be substituted by OH, $OR^1$ or $NR^2R^3$, and which may be interrupted by one or more —O—, —S— or —$NR^4$. Preferably, R is H, OH, linear or branched $C_1$-$C_{18}$ alkyl, $C_5$-$C_7$ cycloalkyl which may be interrupted by one or more —O—, —S— or —$NR^4$—. More preferable, R is H, linear or branched alkyl, cycloalkyl.

When R is divalent, R is substituted or unsubstituted, linear or branched $C_3$-$C_{18}$ alkylene, $C_5$-$C_7$ cycloalkylene which can be substituted by OH, $OR^1$ or $NR^2R^3$, and which may be interrupted by one or more —O—, —S— or —$NR^4$—. Preferably, when R is divalent, R is linear or branched $C_3$-$C_{18}$ alkylene, or $C_5$-$C_7$ cycloalkylene which may be interrupted by one or more —O—, —S— or —$NR^4$—.

When R is trivalent, R is selected from $N(CH_2-CH_2-*)_3$, or

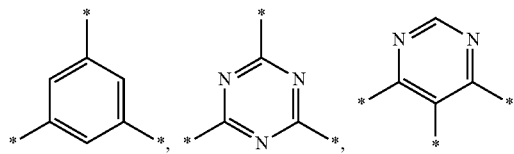

When R is trivalent, R preferably is selected from $N(CH_2-CH_2-*)_3$, or

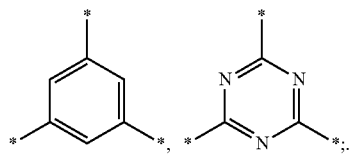

R' is linear or branched $C_1$-$C_5$ alkyl substituted by $NHR^2$, in particular substituted by $NH_2$ or NH(alkyl).

B is a nitrogen containing organic base. Preferably, B is a tertiary amine like triethylamine, tributylamine, tripropylamine, dimethylbenzylamine, N-methyl, N-ethyl, N-cyclohexylmorpholine, N,N,N',N'-tetramethylethylenediamine, N,N,N',N'-tetramethyl-butanediamine, N,N,N',N'-tetramethyl-hexanediamine, pentamethyl-diethylenetriamine, tetramethyl-diaminoethylether, bis (dimethylaminopropyl)-urea, dimethylpiperazine, 1-azabicyclo-(3,3,0)-octane and 1,4-diazabicyclo-(2,2,2)-octane or 1,2-dimethylimidazole, or an amidine, like 2,3-Dimethyl-3,4,5,6-tetrahydropyrimidine, substituted or unsubstituted 1,8-diazabicyclo[5.4.0]undec-7-en (DBU), 1,5-diazabicyclo [4.3.0]non-5-ene (DBN), triazabycyclodecene (TBD), or 1,1,3,3-tetramethylguanidine (TMG), as well as alkanolamine bonds, like triethanolamine, triisopropanolamine, N-methyl- und N-ethyl-diethanolamine and dimethylethanolamine.

L is a $C_1$-$C_8$ substituted or unsubstituted alkylene chain, or a substituted or unsubstituted $C_6$ cycloalkylene chain, or substituted or unsubstituted $C_9$-$C_{11}$ polycyclic chain, or a substituted or unsubstituted double bond, which can be interrupted by O, S, $NR^4$, or a substituted or unsubstituted $C_3$ to $C_4$ alkenylene chain, or a substituted or unsubstituted benzene ring, or substituted or unsubstituted naphthalene ring. Preferably, L is a $C_1$ to $C_8$ substituted or unsubstituted alkylene chain, or a substituted or unsubstituted double bond, or a substituted or unsubstituted $C_3$ to $C_4$ alkenylene chain, or has the formula:

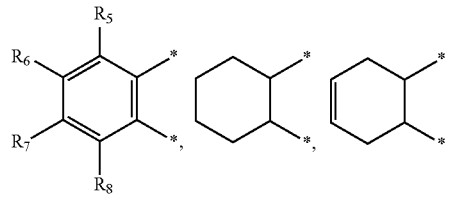

when m is 1 or has the formula:

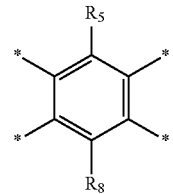

when m is 2.

More preferable, L is a $C_1$ to $C_8$ substituted or unsubstituted alkylene chain, or a substituted or unsubstituted double bond, or a substituted or unsubstituted $C_3$ to $C_4$ alkenylene chain, or has the formula:

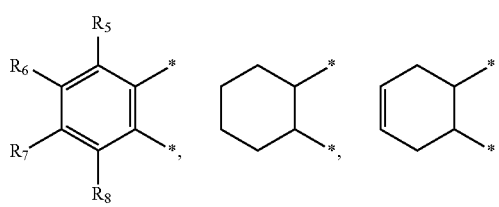

wherein $R^5$, $R^6$, $R^7$, $R^8$ independently from each other are hydrogen, unsubstituted or substituted $C_1$-$C_{28}$ alkyl, $C_2$-$C_{28}$ alkenyl, $C_7$-$C_9$ aralkyl, $C_3$-$C_{20}$ heteroalkyl, $C_5$-$C_{16}$ heteroaralkyl, phenyl or naphthyl, $OR^1$, $NR^2R^3$, or halogen, or $R^7$ and $R^8$, $R^8$ and $R^9$ or $R^9$ and $R^{10}$ are linked together to form 1, 2, 3 or 4 carbocyclic or heterocyclic rings, which may be uninterrupted or interrupted by one or more —O—, —S— or —$NR^4$—. In particular, L is a $C_1$ to $C_8$ substituted or unsubstituted alkylene chain, or has the formula:

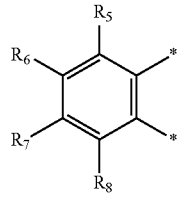

with $R^5$, $R^6$, $R^7$, $R^8$ independently from each other are hydrogen, unsubstituted or substituted $C_1$-$C_{28}$ alkyl, $C_2$-$C_{28}$ alkenyl, $C_7$-$C_9$ aralkyl, $C_3$-$C_{20}$ heteroalkyl, $C_5$-$C_{16}$ heteroaralkyl, phenyl or naphthyl, $OR^1$, $NR^2R^3$, or halogen, or $R^5$ and $R^6$, $R^6$ and $R^7$ or $R^7$ and $R^8$ are linked together to form 1, 2, 3 or 4 carbocyclic or heterocyclic rings, which may be uninterrupted or interrupted by one or more —O—, —S— or —$NR^4$—.

In formula (Ia) od (Ib) or in formula (I'a) or (I'b) or in formula (I"a) or (I"b), $R^1$ is H, $C_1$-$C_{18}$ alkyl.

In formula (Ia) or (Ib) or in formula (I'a) or (I'b) or in formula (I"a) or (I"b), $R^2$ and $R^3$, independently are hydrogen, unsubstituted or substituted $C_1$-$C_{18}$ alkyl or phenyl; or $R^2$ and $R^3$ together with the nitrogen atom to which they are bonded form a 5 or 6 membered-ring which may contain a further heteroatom.

Generally, $R^4$ is H, unsubstituted or substituted $C_1$-$C_{18}$alkyl.

According to the present invention, the ratio between $A_a$ and $B_a$ or between $A_b$ and $B_b$ ranges from 0.5:1 to 10:1, preferably in the range of from 1:1 to 6:1, more preferable in the range of from 1:1 to 4:1.

According to a further embodiment, the present invention is also directed to the compound (C) as disclosed above, wherein the compound is selected from the group consisting of compounds of the general formula (Ia) or (Ib)

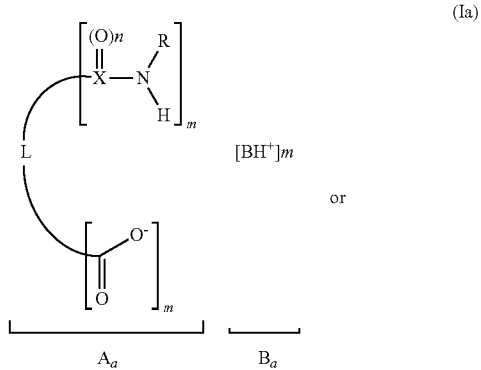

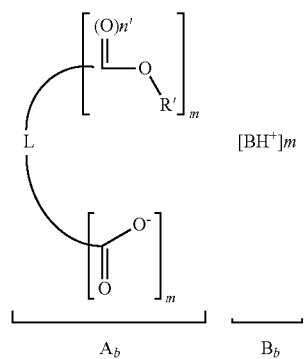

wherein
n is 1 when X is a carbon atom,
n is 2 when X is a sulfur atom,
n' is 0 or 1,
m is 1 or 2,
R is a monovalent, divalent or trivalent rest,
When R is monovalent, R is H, OH, linear or branched $C_1$-$C_{18}$ alkyl, $C_5$-$C_7$ cycloalkyl which may be interrupted by one or more —O—, —S— or —$NR^4$—,
when R is divalent, R is linear or branched $C_3$-$C_{18}$ alkylene, or $C_5$-$C_7$ cycloalkylene which may be interrupted by one or more —O—, —S— or —$NR^4$—,
when R is trivalent, R can be for example the following trivalent residues: $N(CH_2—CH_2—*)_3$,

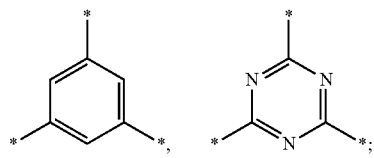

R' is linear or branched alkyl substituted by $NHR^2$,
B is substituted or unsubstituted 1,8-Diazabicyclo[5.4.0]undec-7-en (DBU), 1,5-Diazabicyclo[4.3.0]non-5-ene (DBN), Triazabycyclodecene (TBD), 1,4-Diazabicyclo[2.2.2]octan (DABCO), 1,1,3,3-tetramethylguanidine (TMG), or substituted or unsubstituted tertiary aliphatic amines,
L is a $C_1$ to $C_8$ substituted or unsubstituted alkylene chain, or a substituted or unsubstituted double bond, or a substituted or unsubstituted $C_3$ to $C_4$ alkenylene chain, or has the formula:

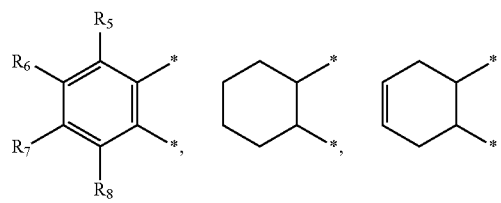

When m is 1 or has the formula:

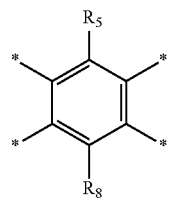

when m is 2

R$^5$, R$^6$, R$^7$, R$^8$ independently from each other are hydrogen, unsubstituted or substituted C$_1$-C$_{28}$ alkyl, C$_2$-C$_{28}$ alkenyl, C$_7$-C$_9$ aralkyl, C$_3$-C$_{20}$ heteroalkyl, C$_5$-C$_{16}$ heteroaralkyl, phenyl or naphthyl, OR$^1$, NR$^2$R$^3$, or halogen, or R$^5$ and R$^6$, R$^6$ and R$^7$ or R$^7$ and R$^8$ are linked together to form 1, 2, 3 or 4 carbocyclic or heterocyclic rings, which may be uninterrupted or interrupted by one or more —O—, —S— or —NR$^4$—;

R$^1$ is H, C$_1$-C$_{18}$ alkyl,

R$^2$, R$^3$, independently are hydrogen, unsubstituted or substituted C$_1$-C$_{18}$alkyl or phenyl, or R$^2$ and R$^3$ together with the nitrogen atom to which they are bonded form a 5 or 6 membered-ring which may contain a further heteroatom, R$^4$ is H, unsubstituted or substituted C$_1$-C$_{18}$ alkyl, the ratio between A$_a$ and B$_a$ or between A$_b$ and B$_b$ ranges from 1:1 to 4:1.

According to a further embodiment, the present invention is also directed to the compound (C) as disclosed above, wherein the compound is selected from the group consisting of compounds of the general formula (I'a) or (I'b)

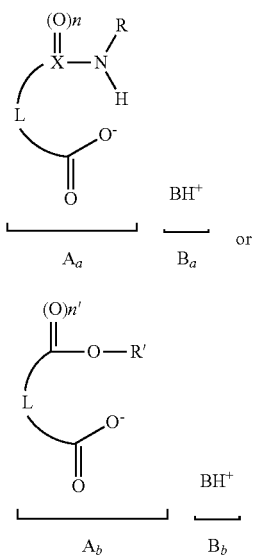

wherein n is 1 when X is a carbon atom, n is 2 when X is a sulfur atom, n' is 0 or 1

R is monovalent,

R is H, linear or branched alkyl, cycloalkyl,

R' is linear or branched alkyl substituted by NH$_2$ or NH(alkyl),

B is DBU, DBN, TBD, DABCO, TMG, tertiary aliphatic amines,

L is a C$_1$ to C$_8$ substituted or unsubstituted alkylene chain, or a substituted or unsubstituted double bond, or a substituted or unsubstituted C$_3$ to C$_4$ alkenylene chain, or has the formula:

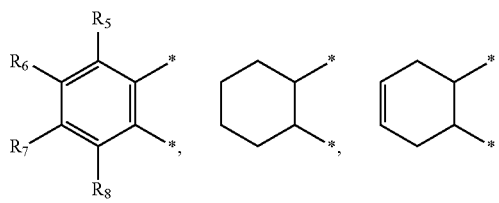

R$^5$, R$^6$, R$^7$, R$^8$ independently from each other are hydrogen, unsubstituted or substituted C$_1$-C$_{28}$ alkyl, C$_2$-C$_{28}$ alkenyl, C$_7$-C$_9$ aralkyl, C$_3$-C$_{20}$ heteroalkyl, C$_5$-C$_{16}$ heteroaralkyl, phenyl or naphthyl, OR$^1$, NR$^2$R$^3$, or halogen, or R$^5$ and R$^6$, R$^6$ and R$^7$ or R$^7$ and R$^8$ are linked together to form 1, 2, 3 or 4 carbocyclic or heterocyclic rings, which may be uninterrupted or interrupted by one or more —O—, —S— or —NR$^4$—;

R$^1$ is H, C$_1$-C$_{18}$alkyl,

R$^2$, R$^3$, independently are hydrogen, unsubstituted or substituted C$_1$-C$_{18}$alkyl or phenyl; or R$^2$ and R$^3$ together with the nitrogen atom to which they are bonded form a 5 or 6 membered-ring which may contain a further heteroatom, R$^4$ is H, unsubstituted or substituted C$_1$-C$_{18}$alkyl, the ratio between A$_a$ and B$_a$ or between A$_b$ and B$_b$ ranges from 1:1 to 4:1.

According to a further embodiment, the present invention is also directed to the compound (C) as disclosed above, wherein the compound is selected from the group consisting of compounds of the general formula (I"a) or (I"b)

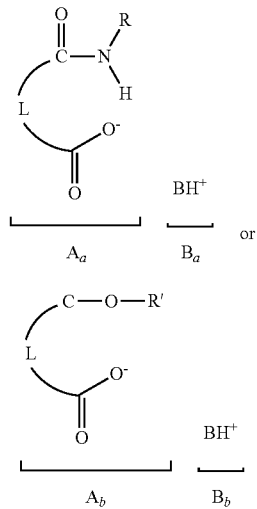

wherein
R is monovalent,
R is H, linear or branched alkyl, cycloalkyl,
R' is linear or branched alkyl substituted by NH$_2$ or NH(alkyl),
B is DBU, DBN, TBD, DABCO, TMG, tertiary aliphatic amines,
L is a C$_1$ to C$_8$ substituted or unsubstituted alkylene chain, or has the formula:

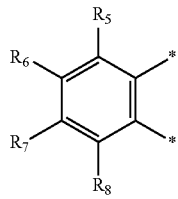

R$^5$, R$^6$, R$^7$, R$^8$ independently from each other are hydrogen, unsubstituted or substituted C$_1$-C$_{28}$ alkyl, C$_2$-C$_{28}$ alkenyl, C$_7$-C$_9$ aralkyl, C$_3$-C$_{20}$ heteroalkyl, C$_5$-C$_{16}$ heteroaralkyl, phenyl or naphthyl, OR$^1$, NR$^2$R$^3$, or halogen,
or
R$^5$ and R$^6$, R$^6$ and R$^7$ or R$^7$ and R$^8$ are linked together to form 1, 2, 3 or 4 carbocyclic or heterocyclic rings, which may be uninterrupted or interrupted by one or more —O—, —S— or —NR$^4$—;
R$^1$ is H, C$_1$-C$_{18}$ alkyl,
R$^2$, R$^3$, independently are hydrogen, unsubstituted or substituted C$_1$-C$_{18}$ alkyl or phenyl; or R$^2$ and R$^3$ together with the nitrogen atom to which they are bonded form a 5 or 6 membered-ring which may contain a further heteroatom,
R$^4$ is H, unsubstituted or substituted C$_1$-C$_{18}$ alkyl,
the ratio between A$_a$ and B$_a$ or between A$_b$ and B$_b$ ranges from 1:1 to 4:1.

According to a further embodiment, the present invention is also directed to the compound (C) as disclosed above, wherein the compound is selected from the group consisting of compounds of the general formula (I"a) or (I"b)

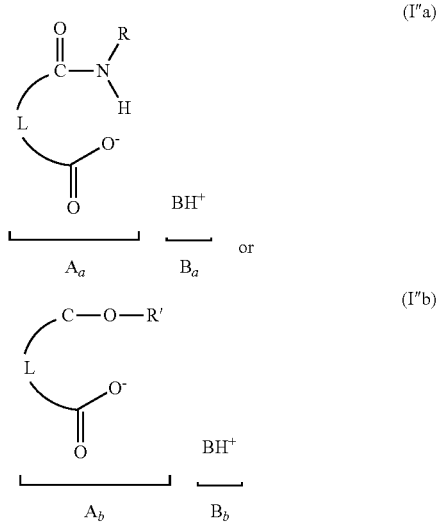

wherein
R is monovalent,
R is H, linear or branched alkyl, cycloalkyl,
R' is linear or branched alkyl substituted by NH$_2$ or NH(alkyl),
B is DBU,
L is a C$_1$ to C$_8$ substituted or unsubstituted alkylene chain, or has the formula:

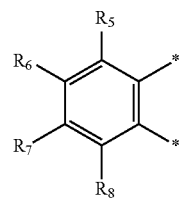

R$^5$, R$^6$, R$^7$, R$^8$ independently from each other are hydrogen, unsubstituted or substituted C$_1$-C$_{28}$ alkyl, C$_2$-C$_{28}$ alkenyl, C$_1$-C$_9$ aralkyl, C$_3$-C$_{20}$ heteroalkyl, C$_5$-C$_{16}$ heteroaralkyl, phenyl or naphthyl, OR$^1$, NR$^2$R$^3$, or halogen,
or
R$^5$ and R$^6$, R$^6$ and R$^7$ or R$^7$ and R$^8$ are linked together to form 1, 2, 3 or 4 carbocyclic or heterocyclic rings, which may be uninterrupted or interrupted by one or more —O—, —S— or —NR$^4$—,
R$^1$ is H, C$_1$-C$_{16}$ alkyl,
R$^2$, R$^3$, independently are hydrogen, unsubstituted or substituted C$_1$-C$_{18}$ alkyl or phenyl; or R$^2$ and R$^3$ together with the nitrogen atom to which they are bonded form a 5 or 6 membered-ring which may contain a further heteroatom,
R$^4$ is H, unsubstituted or substituted C$_1$-C$_{18}$ alkyl,
the ratio between A$_a$ and B$_a$ or between A$_b$ and B$_b$ ranges from 1:1 to 4:1.

The compounds of the present invention can be made by methods well established by the chemical organic synthetic methods. One, non limiting possibility consist in just mixing the base BH and the acidic partner in equimolar quantities in a suitable solvent, for example ethyleneglycol, 1,2-propyleneglycol, 1,4-butanediol, 1,5-pentanediol, and just stir the solution for the required amount of time, for example between 2 hours and 24 hours at a temperature in the range from 10 to 40° C., in particular at room temperature. It is also possible to isolate the salts by working in an appropriate solvent, for example diethylether, tertiobutylmethylether.

It has been found that the compound (C) as defined above can be used as catalyst for the preparation of polyurethanes or epoxy resins.

Compound (C) is especially advantageous for the use as catalyst since it has good solubility in many solvents used in the preparation of polyurethanes or epoxy resins. Methods for preparing polyurethanes and epoxy resins are generally known. According to the present invention, the compound (C) as described above can be used as catalyst in such processes. It is possible to prepare and isolate compound (C) before using it as catalyst. However, it is also possible to prepare the compound (C) in situ, i.e. to add the acidic component as well as the base to the process to be catalyzed.

As set out above, the present invention thus is also directed to a process for preparing a polyurethane comprising reacting at least one polyisocyanate with a polyol composition comprising at least one polyol in the presence of a catalyst composition comprising at least one compound (C) as disclosed above. The compound (C) is particularly suitable as catalyst for preparing molds since it is thermolatent, i.e. it is activated at a predetermined temperature.

Generally, the activation temperature is above 25° C., preferably above 40° C., more preferable above 60° C.

Thus, the process can comprise several steps such as mixing the components and activating the catalyst. The process can comprise further steps, such as temperature treatment or delivering the reaction mixture into a mold.

The present invention is also directed to a process for preparing a polyurethane, wherein the process comprises at least the following steps:
(i) mixing the at least one polyisocyanate, the polyol composition and the compound (C) to obtain a mixture (I);
(ii) delivering the mixture (I) into a mold or to the desired reaction site by pouring, spraying, or distributing;
(iii) heating the mixture (I) to a temperature above 25° C. until the mixture is cured.

Furthermore, the process for preparing a polyurethane according to the present invention can comprise a step selected from reaction injection molding (RIM), reaction transfer molding (RTM), casting molding, vacuum infusion, filament winding, centrifugal casting, long fiber injection, spray coating.

The process according to the present invention is particularly suitable to prepare polyurethane molds, for example fiber reinforced polyurethanes. Therefore the present invention is also directed to a process for preparing a mold comprising a polyurethane according to the present invention.

The compounds used in the process for preparing a polyurethane according to the present invention are exemplified in the following without limiting the scope of the invention.

According to the present invention, the catalyst composition comprises at least one compound (C). It is possible, that the catalyst composition comprises further compounds which can act as a catalyst in a process for preparing polyurethanes. These further compounds might be catalysts generally used in the preparation of polyurethanes or further compounds (C) as defined above. It is also possible in the context of the present invention that the catalyst composition comprises no further compounds, i.e. only comprises compound (C) as catalytically active compound. The catalyst composition further can comprise solvents. Suitable solvents are known to the person skilled in the art.

According to a further embodiment, the present invention is also directed to a process for preparing a polyurethane as disclosed above, wherein the catalyst composition comprises at least one further catalyst.

Suitable further catalysts for preparing the polyurethanes of the present invention, which, in particular, accelerate the reaction between the NCO groups of the diisocyanates and the hydroxyl groups of the polyol are the customary catalysts known from the prior art, for example tertiary amines such as triethylamine, dimethylcyclohexylamine, N-methylmorpholine, N,N'-dimethylpiperazine, diazabicyclo[2.2.2]octane and the like, and also, in particular, organic metal compounds such as titanate esters, iron compounds, tin compounds, e.g. tin diacetate, tin dioctoate, tin dilaurate or the dialkyltin salts of aliphatic carboxylic acids, e.g. dibutyltin diacetate, dibutyltin dilaurate or the like.

In the process of the present invention, at least one polyisocyanate is reacted with a polyol composition comprising at least one polyol.

Suitable polyisocyanates are known to the person skilled in the art. As polyisocyanates it is possible to use aliphatic, cycloaliphatic, araliphatic and/or aromatic diisocyanates. Specific examples include the following aromatic isocyanates: 2,4-tolylene diisocyanate, mixtures of 2,4- and 2,6-toluene diisocyanate, 4,4'-, 2,4'- and/or 2,2'-diphenylmethane diisocyanate (MDI), mixtures of 2,4'- and 4,4'-diphenylmethane diisocyanate, urethane-modified liquid 4,4'- and/or 2,4-diphenylmethane diisocyanates, 4,4'-diisocyanatodiphenylethane, the mixtures of monomeric methanediphenyl diisocyanates and more highly polycyclic homologues of methanediphenyl diisocyanate (polymeric MDI), 1,2- and 1,5-naphthylene diisocyanate.

Aliphatic diisocyanates used are customarily aliphatic and/or cycloaliphatic diisocyanates, examples being tri-, tetra-, penta-, hexa-, hepta- and/or octamethylene diisocyanate, 2-methylpentamethylene 1,5-diisocyanate, 2-ethylbutylene 1,4-diisocyanate, 1-isocyanato-3,3,5-trimethyl-5-isocyanatomethylcyclohexane (isophorone diisocyanate, IPDI), 1,4- and/or 1,3-bis(isocyanatomethyl)cyclohexane (HXDI), 1,4-cyclohexane diisocyanate, 1-methyl-2,4- and/or -2,6-cyclohexane diisocyanate, 4,4'-, 2,4'- and/or 2,2'-dicyclohexylmethane diisocyanate.

Polyisocyanate prepolymers are obtainable by reacting above-described polyisocyanates in excess, at temperatures of 30 to 100° C., for example, preferably at about 80° C., with polyols to give the prepolymer. For the preparation of the prepolymers of the invention, preference is given to using polyisocyanates and commercial polyols based on polyesters, starting for example from adipic acid, or on polyethers, starting for example from ethylene oxide and/or propylene oxide.

Polyols are known to the skilled person and are described for example in "Kunststoffhandbuch, volume 7, Polyurethane", Carl Hanser Verlag, 3rd edition 1993, section 3.1. Polyols used with preference in this context are the polymeric compounds described under b), having hydrogen atoms that are reactive toward isocyanates. Particularly preferred for use as polyols are polyetherols.

In the preparation of the isocyanate prepolymers, customary chain extenders or crosslinking agents are added optionally to the stated polyols. Such substances are described above hereinafter. Particularly preferred for use as chain extender is 1,4-butanediol, dipropylene glycol and/or tripropylene glycol. In this case the ratio of organic polyisocyanates to polyols and chain extenders is preferably selected such that the isocyanate prepolymer has an NCO content of 2% to 30%, preferably of 6% to 28%, more preferably of 10% to 24%.

Particularly preferred polyisocyanates are selected from the group consisting of MDI, polymeric MDI, and TDI, and also derivatives thereof or prepolymers of these polyisocyanates.

According to a further embodiment, the present invention therefore is also directed to a process for preparing a polyurethane as disclosed above, wherein the polyisocyanate is selected from the group consisting of MDI, polymeric MDI, and TDI, and derivatives thereof or prepolymers of these polyisocyanates.

The polyol composition comprises at least one polyol. Suitable polyols are known to the person skilled in the art. Suitable polyols are for example polyols having a functionality of from 2 to 4 and molecular weights of from 500 g/mol to 8000 g/mol. Compounds which have been found to be useful are particularly polyether diols or polyester diols. Also suitable are other hydroxyl-containing polymers having ether or ester groups in the polymer chain, for example polyacetals such as polyoxymethylene and in particular water-insoluble formals, eg. polybutanediol formal and polyhexanediol formal, and polycarbonates, in particular those prepared from diphenyl carbonate and 1,6-hexanediol by transesterification. The polyhydroxyl compounds should be at least predominantly linear and have to be essentially difunctional in the context of the isocyanate reaction. The polyhydroxyl compounds mentioned can be used as individual compounds or in the form of mixtures.

Suitable polyether diols can be prepared by known methods, for example from one or more alkylene oxides having from 2 to 4 carbon atoms in the alkylene radical by anionic polymerization using alkali metal hydroxides such as sodium or potassium hydroxide, or alkali metal alkoxides such as sodium methoxide, sodium or potassium ethoxide or potassium isopropoxide as catalysts and with addition of at least one initiator molecule containing 2 or 3, preferably 2, reactive hydrogen atoms in bonded form, or by cationic polymerization using Lewis acids such as antimony pentachloride, boron fluoride etherate, etc., or bleaching earth as catalysts.

Examples of suitable alkylene oxides are tetrahydrofuran, 1,3-propylene oxide, 1,2- or 2,3-butylene oxide and particularly preferably ethylene oxide and 1,2-propylene oxide. The alkylene oxides can be used individually, alternately in succession or as mixtures. Examples of suitable initiator molecules are: water, organic dicarboxylic acids such as succinic acid, adipic acid and/or glutaric acid, alkanolamines such as ethanolamine, N-alkylalkanol-amines, N-alkyldialkanolamines such as N-methyldiethanolamine and N-ethyldiethanolamine and preferably dihydric alcohols which may contain bonded ether bridges, e.g. ethanediol, 1,2- and 1,3-propanediol, 1,4-butanediol, diethylene glycol, 1,5-pentanediol, 1,6-hexanediol, dipropylene glycol, 2-methylpentane-1,5-diol and 2-ethylbutane-1,4-diol. The initiator molecules can be used individually or as mixtures.

Preference is given to using polyetherols derived from 1,2-propylene oxide and ethylene oxide. Such polyetherols can be obtained by, for example, polymerizing first the 1,2-propylene oxide and subsequently thereto the ethylene oxide onto the initiator molecule or first copolymerizing all the 1,2-propylene oxide together with part of the ethylene oxide and subsequently polymerizing on the remainder of the ethylene oxide or, stepwise, first polymerizing part of the ethylene oxide, then all the 1,2-propylene oxide.

Other particularly suitable polyetherols are the hydroxyl-containing polymerization products of tetrahydrofuran.

The essentially linear polyetherols usually have molecular weights of from 500 g/mol to 8000 g/mol, preferably from 600 g/mol to 6000 g/mol and in particular from 650 g/mol to 3500 g/mol, with the polyoxytetramethylene glycols preferably having molecular weights of from 500 g/mol to 2800 g/mol. They can be used either individually or in the form of mixtures with one another.

Suitable polyester diols can be prepared, for example, from dicarboxylic acids having from 2 to 12, preferably from 4 to 6, carbon atoms and diols. Examples of suitable dicarboxylic acids are: aliphatic dicarboxylic acids such as succinic acid, glutaric acid, adipic acid, suberic acid, azelaic acid and sebacic acid, and aromatic dicarboxylic acids such as phthalic acid, isophthalic acid and terephthalic acid. The dicarboxylic acids can be used individually or as mixtures, e.g. in the form of a succinic, glutaric and adipic acid mixture. For preparing the polyesterols, it may be advantageous to replace the dicarboxylic acids with the corresponding dicarboxylic acid derivatives such as monoesters or diesters of dicarboxylic acid having from 1 to 4 carbon atoms in the alcohol radical, dicarboxylic anhydrides or dicarboxylic acid dichlorides. Examples of diols are glycols having from 2 to 10, preferably from 2 to 6, carbon atoms, for example ethylene glycol, diethylene glycol, 1,4-butanediol, 1,5-pentanediol, 1,6-hexanediol, 1,10-decanediol, 2,2-dimethylpropane-1,3-diol, 1,3-propanediol and dipropylene glycol. Depending on the desired properties, the diols can be used alone or in admixture with one another.

Also suitable are esters of carbonic acid with the diols mentioned, in particular those having from 4 to 6 carbon atoms, e.g. 1,4-butanediol and/or 1,6-hexanediol; condensation products of omega-hydroxycarboxylic acids, for example omega-hydroxycaproic acid, and preferably polymerization products of lactones, for example unsubstituted or substituted epsilon-caprolactone.

Polyester diols which are preferably used are ethanediol polyadipates, 1,4-butanediol polyadipates, ethanediol-1,4-butanediol polyadipates, 1,6-hexanediol-neopentyl glycol polyadipates, 1,6-hexanediol-1,4-butanediol polyadipates and polycaprolactones.

The polyester diols generally have molecular weights of from 500 g/mol to 6000 g/mol, preferably from 600 g/mol to 3500 g/mol.

Furthermore, depending on the nature of the polyurethane prepared, the polyol composition may comprise low molecular weight chain extenders and crosslinkers and also further auxiliaries and additives.

Suitable crosslinkers are known to the person skilled in the art.

Suitable chain extenders having molecular weights of generally from 60 g/mol to 400 g/mol, preferably from 60 g/mol to 300 g/mol, are preferably aliphatic diols having from 2 to 12 carbon atoms, preferably having 2, 4 or 6 carbon atoms, e.g. ethanediol, 1,6-hexanediol, diethylene glycol, dipropylene glycol and in particular 1,4-butanediol. However, other suitable chain extenders are diesters of terephthalic acid with glycols having from 2 to 4 carbon atoms, e.g. bis(ethylene glycol) terephthalate or bis(1,4-butanediol) terephthalate and hydroxyalkylene ethers of hydroquinone, e.g. 1,4-di(beta-hydroxyethyl) hydroquinone and also polytetramethylene glycols.

Depending on the desired properties of the polyurethanes of the present invention, the amounts of the higher molecular weight polyols and the chain extenders and/or crosslinkers which are used can be varied within a relatively wide range of molar ratios. In the case of the TPUs preferably prepared, this enables the hardness and melt flow index to be adjusted, with the hardness and the melt viscosity rising with an increasing content of chain extenders (c), while the melt flow index falls.

A blowing agent may be present when it is desirable to produce a cellular product. Suitable chemical and physical blowing agents are known to the person skilled in the art.

The polyisocyanate and the polyolcomposition can be reacted at an isocyanate index of from 70 to 1000 or more, although a more typical isocyanate index is from 80 to 500. Isocyanate index is calculated as the number of reactive isocyanate groups provided by the polyisocyanate component divided by the number of isocyanate-reactive groups in the polyol composition (including isocyanate-reactive blowing agents such as water, if present) and multiplying by 100. Water is considered to have two isocyanate-reactive groups per molecule for purposes of calculating isocyanate index. A preferred isocyanate index is from 100 to 300.

The catalyst composition is used in catalytically sufficient amounts. A suitable amount of the catalyst mixture is from about 0.02 to about 2 parts, especially from about 0.05 to about 0.5 part, of the catalyst mixture per 100 parts by weight of the polyol(s). The weight of any solvent is disregarded in determining the amount of catalyst composition.

In accordance with the invention it is possible to add customary auxiliaries. Examples that may be mentioned include surface-active substances, fillers, further flame retardants, nucleators, oxidation stabilizers, lubricity aids and mold release aids, dyes and pigments, optionally stabilizers, with respect to hydrolysis, light, heat, or discoloration, for example, inorganic and/or organic fillers, reinforcing agents, and plasticizers. Suitable auxiliaries and adjuvants may be found, for example, in Kunststoffhandbuch, volume VII, edited by Vieweg and Höchtlen, Carl Hanser Verlag, Munich 1966 (pp. 103-113).

According to a further aspect, the present invention is also directed to the use of the compound (C) as disclosed above as catalyst in a process for the preparation of a polyurethane.

Furthermore, the present invention is also directed to a polyurethane obtained or obtainable according to a process as disclosed above. The polyurethanes according to the present invention are particularly suitable as matrix material for fiber reinforced composites. They have for example improve matrix dominated properties like fatigue or inter laminar shear strength (ILSS).

The polyurethanes obtained according to the present invention are in particular suitable for applications such as coatings, laminating, seals, and production of moldings for applications in which components of very high surface area are being produced, such as rotor blades for wind turbines, boat hulls, or plastic vehicle bodies for automobiles.

Further embodiments of the present invention are apparent from the claims and the examples. It is understood that the features of the subject matter/method/uses of the invention, as elucidated below and as stated above, can be used not only in the particular combination specified but also in other combinations as well, without departing the scope of the invention. Accordingly, for example, the combination of a preferred feature with a more preferred feature, or of an otherwise uncharacterized feature with a very preferred feature, etc., is implicitly comprised, even if that combination is not expressly mentioned.

Listed below are exemplary embodiments of the present invention, which do not restrict the present invention. In particular, the present invention also encompasses embodiments which arise from the dependency references stated below, and hence combinations.

1. Compound (C) selected from the group consisting of compounds of the general formula (Ia) or (Ib)

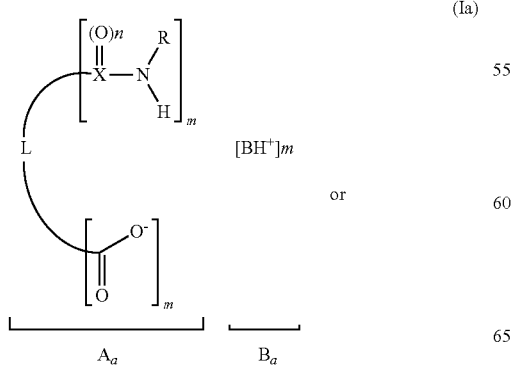

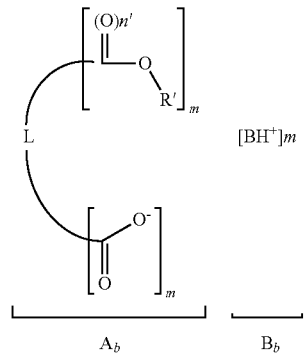

wherein
n is 0 or 1 when X is a carbon atom,
n is 2 when X is a sulfur atom,
n' is 0 or 1,
m is an integer from 1 to 6,
R is selected from monovalent, or divalent, or trivalent or polyvalent residues, wherein
  when R is monovalent, R is H, OH, substituted or unsubstituted, linear or branched $C_1$-$C_{18}$ alkyl, $C_5$-$C_7$ cycloalkyl which can be substituted by OH, $OR^1$ or $NR^2R^3$, and which may be interrupted by one or more —O—, —S— or —$NR^4$—;
  when R is divalent, R is substituted or unsubstituted, linear or branched $C_3$-$C_{18}$ alkylene, $C_5$-$C_7$ cycloalkylene which can be substituted by OH, $OR^1$ or $NR^2R^3$, and which may be interrupted by one or more —O—, —S— or —$NR^4$—;
  when R is trivalent, R is selected from N(CH$_2$—CH$_2$—*)$_3$,

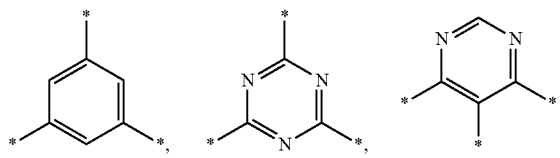

R' is linear or branched $C_1$-$C_5$ alkyl substituted by $NHR^2$,
B is a nitrogen containing organic base,
L is a $C_1$-$C_8$ substituted or unsubstituted alkylene chain, or a substituted or unsubstituted $C_6$ cycloalkylene chain, or substituted or unsubstituted $C_9$-$C_{11}$ polycyclic chain, or a substituted or unsubstituted double bond, which can be interrupted by O, S, $NR^4$, or a substituted or unsubstituted $C_3$ to $C_4$ alkenylene chain, or a substituted or unsubstituted benzene ring, or substituted or unsubstituted naphthalene ring,
$R^1$ is H, $C_1$-$C_{18}$ alkyl,
$R^2$ and $R^3$, independently are hydrogen, unsubstituted or substituted $C_1$-$C_{18}$ alkyl or phenyl; or $R^2$ and $R^3$ together with the nitrogen atom to which they are bonded form a 5 or 6 membered-ring which may contain a further heteroatom,
$R^4$ is H, unsubstituted or substituted $C_1$-$C_{18}$ alkyl,
the ratio between $A_a$ and $B_a$ or between $A_b$ and $B_b$ ranges from 0.5:1 to 10:1.

2. Compound (C) selected from the group consisting of compounds of the general formula (Ia) or (Ib)

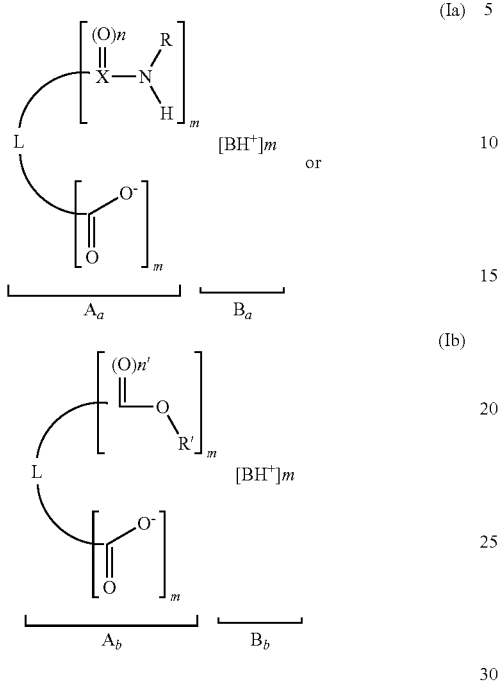

wherein
n is 0 or 1 when X is a carbon atom,
n is 2 when X is a sulfur atom,
n' is 0 or 1,
m is an integer from 1 to 6,
R is selected from monovalent, or divalent, or trivalent or polyvalent residues, wherein
  when R is monovalent, R is H, OH, substituted or unsubstituted, linear or branched $C_1$-$C_{18}$ alkyl, $C_5$-$C_7$ cycloalkyl which can be substituted by OH, $OR^1$ or $NR^2R^3$, and which may be interrupted by one or more —O—, —S— or —$NR^4$—;
  when R is divalent, R is substituted or unsubstituted, linear or branched $C_3$-$C_{18}$ alkylene, $C_5$-$C_7$ cycloalkylene which can be substituted by OH, $OR^1$ or $NR^2R^3$, and which may be interrupted by one or more —O—, —S— or —$NR^4$—;
  when R is trivalent, R is selected from $N(CH_2—CH_2—*)_3$,

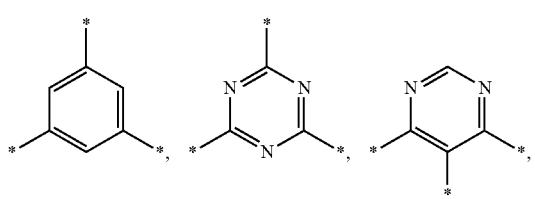

R' is linear or branched $C_1$-$C_5$ alkyl substituted by $NHR^2$,
B is a nitrogen containing organic base,
L is a $C_1$-$C_8$ substituted or unsubstituted alkylene chain, or a substituted or unsubstituted $C_6$ cycloalkylene chain, or substituted or unsubstituted $C_9$-$C_{11}$ polycyclic chain, or a substituted or unsubstituted double bond, which can be interrupted by O, S, $NR^4$, or a substituted or unsubstituted $C_3$ to $C_4$ alkenylene chain, or a substituted or unsubstituted benzene ring, or substituted or unsubstituted naphthalene ring,
$R^1$ is H, $C_1$-$C_{18}$ alkyl,
$R^2$ and $R^3$, independently are hydrogen, unsubstituted or substituted $C_1$-$C_{18}$ alkyl or phenyl; or $R^2$ and $R^3$ together with the nitrogen atom to which they are bonded form a 5 or 6 membered-ring which may contain a further heteroatom,
$R^4$ is H, unsubstituted or substituted $C_1$-$C_{18}$ alkyl,
the ratio between $A_a$ and $B_a$ or between $A_b$ and $B_b$ ranges from 1:1 to 4:1.

3. The compound (C) according to embodiment 1 or 2, wherein the compound is selected from the group consisting of compounds of the general formula (Ia) or (Ib)

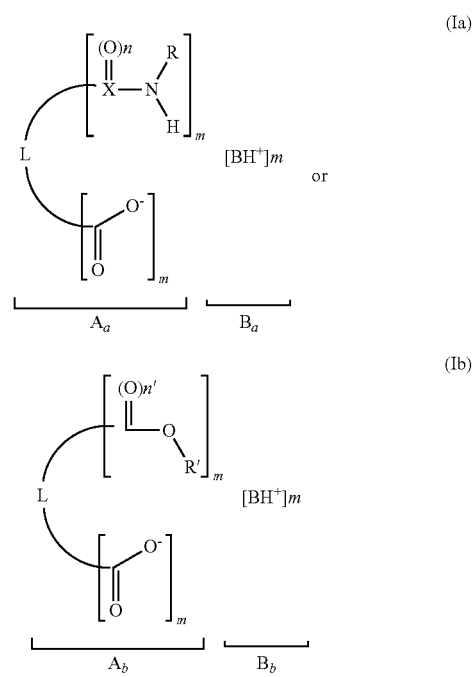

wherein
n is 1 when X is a carbon atom,
n is 2 when X is a sulfur atom,
n' is 0 or 1,
m is 1 or 2,
R is a monovalent, divalent or trivalent rest,
  when R is monovalent, R is H, OH, linear or branched $C_1$-$C_{18}$ alkyl, $C_5$-$C_7$ cycloalkyl which may be interrupted by one or more —O—, —S— or —$NR^4$—,
  when R is divalent, R is linear or branched $C_3$-$C_{18}$ alkylene, or $C_5$-$C_7$ cycloalkylene which may be interrupted by one or more —O—, —S— or —$NR^4$—,
  when R is trivalent, R can be for example the following trivalent residues: $N(CH_2—CH_2—*)_3$,

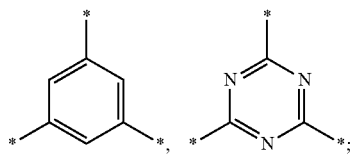

R' is linear or branched alkyl substituted by NHR$^2$,

B is substituted or unsubstituted 1,8-Diazabicyclo[5.4.0]undec-7-en (DBU), 1,5-Diazabicyclo[4.3.0]non-5-ene (DBN), Triazabycyclodecene (TBD), 1,4-Diazabicyclo[2.2.2]octan (DABCO), 1,1,3,3-tetramethylguanidine (TMG), or substituted or unsubstituted tertiary aliphatic amines, $C_1$-$C_5$ to $C_8$ substituted or unsubstituted alkylene chain, or a substituted or unsubstituted double bond, or a substituted or unsubstituted $C_3$ to $C_4$ alkenylene chain, or has the formula:

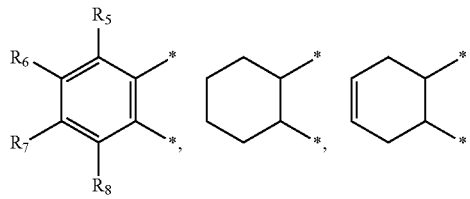

when m is 1 or has the formula:

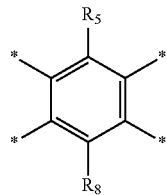

when m is 2

$R^5$, $R^6$, $R^7$, $R^8$ independently from each other are hydrogen, unsubstituted or substituted $C_1$-$C_{28}$alkyl, $C_2$-$C_{28}$alkenyl, $C_7$-$C_9$aralkyl, $C_3$-$C_{20}$ heteroalkyl, $C_5$-$C_{16}$heteroaralkyl, phenyl or naphthyl, $OR^1$, $NR^2R^3$, or halogen, or $R^5$ and $R^6$, $R^6$ and $R^7$ or $R^7$ and $R^8$ are linked together to form 1, 2, 3 or 4 carbocyclic or heterocyclic rings, which may be uninterrupted or interrupted by one or more —O—, —S— or —NR$^4$—;

$R^1$ is H, $C_1$-$C_{18}$ alkyl, $R^2$, $R^3$, independently are hydrogen, unsubstituted or substituted $C_1$-$C_{18}$alkyl or phenyl, or $R^2$ and $R^3$ together with the nitrogen atom to which they are bonded form a 5 or 6 membered-ring which may contain a further heteroatom, $R^4$ is H, unsubstituted or substituted $C_1$-$C_{18}$alkyl, the ratio between $A_a$ and $B_a$ or between $A_b$ and $B_b$ ranges from 1:1 to 4:1.

4. The compound (C) according to any of embodiments 1 to 3, wherein the compound is selected from the group consisting of compounds of the general formula (I'a) or (I'b)

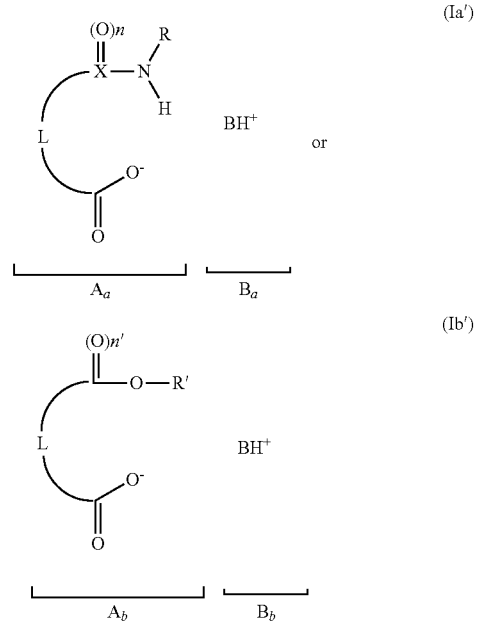

wherein
n is 1 when X is a carbon atom,
n is 2 when X is a sulfur atom,
n' is 0 or 1,
R is monovalent,
R is H, linear or branched alkyl, cycloalkyl,
R' is linear or branched alkyl substituted by NH$_2$ or NH(alkyl),
B is DBU, DBN, TBD, DABCO, TMG, tertiary aliphatic amines,
L is a $C_1$ to $C_8$ substituted or unsubstituted alkylene chain, or a substituted or unsubstituted double bond, or a substituted or unsubstituted $C_3$ to $C_4$ alkenylene chain, or has the formula:

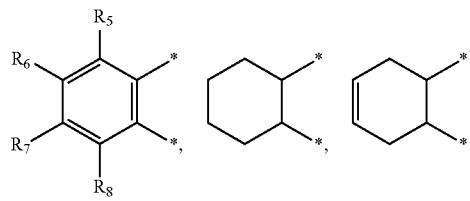

$R^5$, $R^6$, $R^7$, $R^8$ independently from each other are hydrogen, unsubstituted or substituted $C_1$-$C_{28}$alkyl, $C_2$-$C_{28}$alkenyl, $C_7$-$C_9$aralkyl, $C_3$-$C_{20}$heteroalkyl, $C_5$-$C_{16}$heteroaralkyl, phenyl or naphthyl, $OR^1$, $NR^2R^3$, or halogen, or $R^5$ and $R^6$, $R^6$ and $R^7$ or $R^7$ and $R^8$ are linked together to form 1, 2, 3 or 4 carbocyclic or heterocyclic rings, which may be uninterrupted or interrupted by one or more —O—, —S— or —NR$^4$—;

$R^1$ is H, $C_1$-$C_{18}$alkyl, $R^2$, $R^3$, independently are hydrogen, unsubstituted or substituted $C_1$-$C_{18}$alkyl or phenyl; or $R^2$ and $R^3$ together with the nitrogen atom to which they are bonded form a 5 or 6 membered-ring which may contain a further heteroatom, $R^4$ is H, unsubstituted or substituted $C_1$-$C_{18}$alkyl, the ratio between $A_a$ and $B_a$ or between $A_b$ and $B_b$ ranges from 1:1 to 4:1.

5. The compound (C) according to any of embodiments 1 to 4, wherein the compound is selected from the group consisting of compounds of the general formula (I"a) or (I"b)

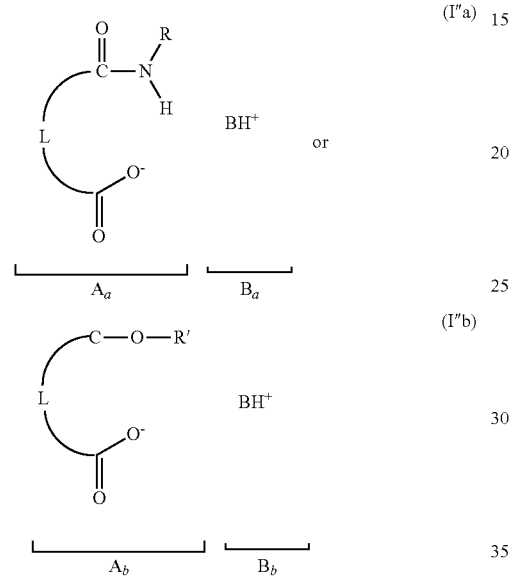

wherein
R is monovalent,
R is H, linear or branched alkyl, cycloalkyl,
R' is linear or branched alkyl substituted by $NH_2$ or NH(alkyl),
B is DBU, DBN, TBD, DABCO, TMG, tertiary aliphatic amines,
L is a $C_1$ to $C_8$ substituted or unsubstituted alkylene chain, or has the formula:

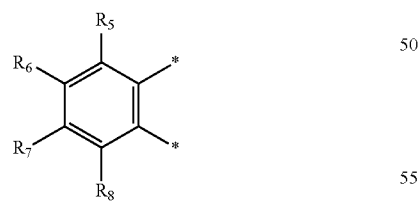

$R^5$, $R^6$, $R^7$, $R^8$ independently from each other are hydrogen, unsubstituted or substituted $C_1$-$C_{28}$alkyl, $C_2$-$C_{28}$alkenyl, $C_7$-$C_9$aralkyl, $C_3$-$C_{20}$heteroalkyl, $C_5$-$C_{16}$heteroaralkyl, phenyl or naphthyl, $OR^1$, $NR^2R^3$, or halogen,
or
$R^5$ and $R^6$, $R^6$ and $R^7$ or $R^7$ and $R^8$ are linked together to form 1, 2, 3 or 4 carbocyclic or heterocyclic rings, which may be uninterrupted or interrupted by one or more —O—, —S— or —$NR^4$—;

$R^1$ is H, $C_1$-$C_{18}$ alkyl, $R^2$, $R^3$, independently are hydrogen, unsubstituted or substituted $C_1$-$C_{18}$alkyl or phenyl; or $R^2$ and $R^3$ together with the nitrogen atom to which they are bonded form a 5 or 6 membered-ring which may contain a further heteroatom, $R^4$ is H, unsubstituted or substituted $C_1$-$C_{18}$alkyl, the ratio between $A_a$ and $B_a$ or between $A_b$ and $B_b$ ranges from 1:1 to 4:1.

6. The compound (C) according to any of embodiments 1 to 5, wherein the compound is selected from the group consisting of compounds of the general formula (I"a) or (I"b)

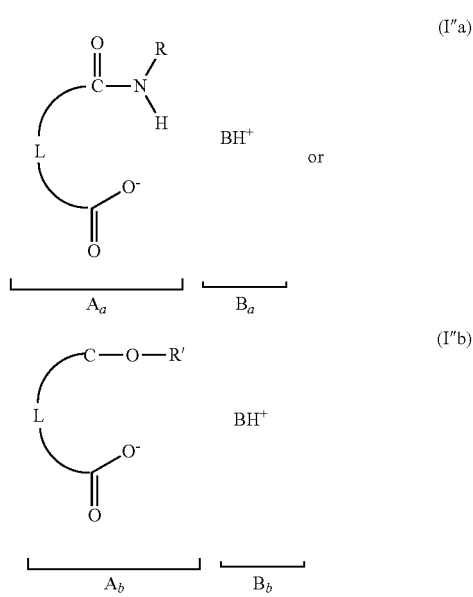

wherein
R is monovalent,
R is H, linear or branched alkyl, cycloalkyl,
R' is linear or branched alkyl substituted by $NH_2$ or NH(alkyl),
B is DBU,
L is a $C_1$ to $C_8$ substituted or unsubstituted alkylene chain, or has the formula:

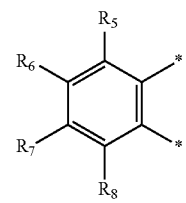

$R^5$, $R^6$, $R^7$, $R^8$ independently from each other are hydrogen, unsubstituted or substituted $C_1$-$C_{28}$alkyl, $C_2$-$C_{28}$alkenyl, $C_1$-$C_9$aralkyl, $C_3$-$C_{20}$heteroalkyl, $C_5$-$C_{16}$heteroaralkyl, phenyl or naphthyl, $OR^1$, $NR^2R^3$, or halogen, or
R⁵ and R⁶, R⁶ and R⁷ or R⁷ and R⁸ are linked together to form 1, 2, 3 or 4 carbocyclic or heterocyclic rings, which may be uninterrupted or interrupted by one or more —O—, —S— or —NR⁴—, R¹ is H, $C_1$-$C_{16}$alkyl, R², R³, independently are hydrogen, unsubstituted or substituted $C_1$-$C_{18}$alkyl or phenyl; or R² and R³ together with the nitrogen atom to which they are bonded form a 5 or 6 membered-ring which may contain a further heteroatom, R⁴ is H, unsubstituted or substituted $C_1$-$C_{18}$alkyl, the ratio between $A_a$ and $B_a$ or between $A_b$ and $B_b$ ranges from 1:1 to 4:1.

7. Process for preparing a polyurethane comprising reacting at least one polyisocyanate with a polyol composition comprising at least one polyol in the presence of a catalyst composition comprising at least one compound (C) according to embodiment 1.

8. Process for preparing a polyurethane comprising reacting at least one polyisocyanate with a polyol composition comprising at least one polyol in the presence of a catalyst composition comprising at least one compound (C) according to embodiment 2.

9. Process for preparing a polyurethane comprising reacting at least one polyisocyanate with a polyol composition comprising at least one polyol in the presence of a catalyst composition comprising at least one compound (C) according to embodiment 3.

10. Process for preparing a polyurethane comprising reacting at least one polyisocyanate with a polyol composition comprising at least one polyol in the presence of a catalyst composition comprising at least one compound (C) according to embodiment 4.

11. Process for preparing a polyurethane comprising reacting at least one polyisocyanate with a polyol composition comprising at least one polyol in the presence of a catalyst composition comprising at least one compound (C) according to embodiment 5.

12. Process for preparing a polyurethane comprising reacting at least one polyisocyanate with a polyol composition comprising at least one polyol in the presence of a catalyst composition comprising at least one compound (C) according to embodiment 6.

13. The process according to any of embodiments 7 to 12, wherein the catalyst composition comprises at least one further catalyst.

14. The process according to any of embodiments 7 to 13, wherein the polyisocyanate is selected from the group consisting of MDI, polymeric MDI, and TDI, and derivatives thereof or prepolymers of these polyisocyanates.

15. Use of the compound (C) according to any of embodiments 1 to 6 as catalyst in a process for the preparation of a polyurethane or epoxy resin.

16. Process for preparing a polyurethane comprising reacting at least one polyisocyanate with a polyol composition comprising at least one polyol in the presence of a catalyst composition comprising at least one compound (C) selected from the group consisting of compounds of the general formula (Ia) or (Ib)

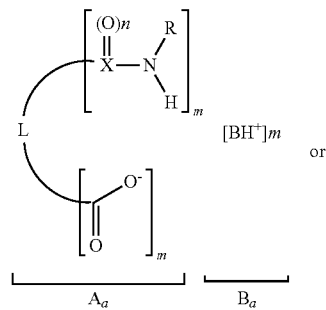

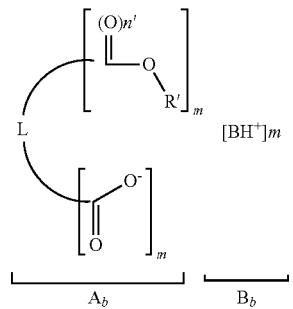

wherein
n is 0 or 1 when X is a carbon atom,
n is 2 when X is a sulfur atom,
n' is 0 or 1,
m is an integer from 1 to 6,
R is selected from monovalent, or divalent, or trivalent or polyvalent residues, wherein
when R is monovalent, R is H, OH, substituted or unsubstituted, linear or branched $C_1$-$C_{18}$ alkyl, $C_5$-$C_7$ cycloalkyl which can be substituted by OH, OR¹ or NR²R³, and which may be interrupted by one or more —O—, —S— or —NR⁴—;
when R is divalent, R is substituted or unsubstituted, linear or branched $C_3$-$C_{18}$ alkylene, $C_5$-$C_7$ cycloalkylene which can be substituted by OH, OR¹ or NR²R³, and which may be interrupted by one or more —O—, —S— or —NR⁴—;
when R is trivalent, R is selected from N(CH₂—CH₂—*)₃,

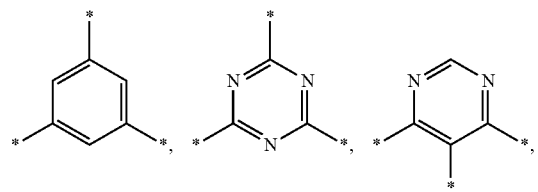

R' is linear or branched $C_1$-$C_5$ alkyl substituted by NHR²,
B is a nitrogen containing organic base,
L is a $C_1$-$C_8$ substituted or unsubstituted alkylene chain, or a substituted or unsubstituted $C_6$ cycloalkylene chain, or substituted or unsubstituted $C_9$-$C_{11}$ polycyclic chain, or a substituted or unsubstituted double bond, which can be interrupted by O, S, NR⁴, or a substituted or unsubstituted $C_3$ to $C_4$ alkenylene chain, or a substituted or unsubstituted benzene ring, or substituted or unsubstituted naphthalene ring, R$_1$ is H, C$_1$-C$_{18}$ alkyl, R$^2$ and R$^3$, independently are hydrogen, unsubstituted or substituted C$_1$-C$_{18}$ alkyl or phenyl; or R$^2$ and R$^3$ together with the nitrogen atom to which they are bonded form a 5 or 6 membered-ring which may contain a further heteroatom, R$^4$ is H, unsubstituted or substituted C$_1$-C$_{18}$ alkyl, the ratio between A$_a$ and B$_a$ or between A$_b$ and B$_b$ ranges from 0.5:1 to 10:1.

17. Process for preparing a epoxy resin, wherein the process is carried out in the presence of a catalyst composition comprising at least one compound (C) selected from the group consisting of compounds of the general formula (Ia) or (Ib)

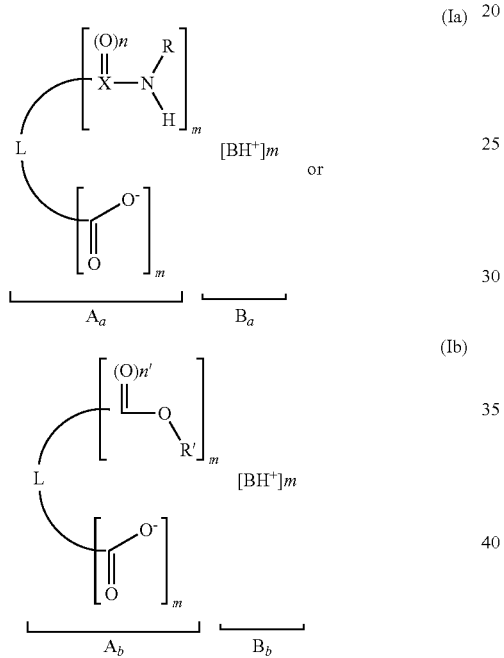

wherein n is 0 or 1 when X is a carbon atom, n is 2 when X is a sulfur atom, n' is 0 or 1, m is an integer from 1 to 6, R is selected from monovalent, or divalent, or trivalent or polyvalent residues, wherein when R is monovalent, R is H, OH, substituted or unsubstituted, linear or branched C$_1$-C$_{18}$ alkyl, C$_5$-C$_7$ cycloalkyl which can be substituted by OH, OR$^1$ or NR$^2$R$^3$, and which may be interrupted by one or more —O—, —S— or —NR$^4$—;

when R is divalent, R is substituted or unsubstituted, linear or branched C$_3$-C$_{18}$ alkylene, C$_5$-C$_7$ cycloalkylene which can be substituted by OH, OR$^1$ or NR$^2$R$^3$, and which may be interrupted by one or more —O—, —S— or —NR$^4$—;

when R is trivalent, R is selected from N(CH$_2$—CH$_2$—*)$_3$,

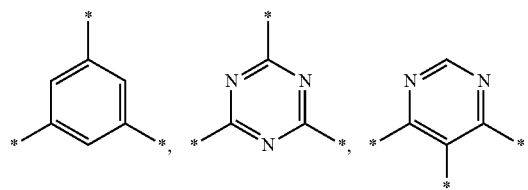

R' is linear or branched C$_1$-C$_5$ alkyl substituted by NHR$^2$,

B is a nitrogen containing organic base,

L is a C$_1$-C$_8$ substituted or unsubstituted alkylene chain, or a substituted or unsubstituted C$_6$ cycloalkylene chain, or substituted or unsubstituted C$_9$-C$_{11}$ polycyclic chain, or a substituted or unsubstituted double bond, which can be interrupted by O, S, NR$^4$, or a substituted or unsubstituted C$_3$ to C$_4$ alkenylene chain, or a substituted or unsubstituted benzene ring, or substituted or unsubstituted naphthalene ring, R$^1$ is H, C$_1$-C$_{18}$ alkyl, R$^2$ and R$^3$, independently are hydrogen, unsubstituted or substituted C$_1$-C$_{18}$ alkyl or phenyl; or R$^2$ and R$^3$ together with the nitrogen atom to which they are bonded form a 5 or 6 membered-ring which may contain a further heteroatom, R$^4$ is H, unsubstituted or substituted C$_1$-C$_{18}$ alkyl, the ratio between A$_a$ and B$_a$ or between A$_b$ and B$_b$ ranges from 0.5:1 to 10:1.

The examples which follow are for illustration of the invention, but are not in any way restricting as regards the subject matter of the present invention.

EXAMPLES

I. Preparation of Catalysts

Non limiting examples of the inventive compounds are given below. The respective structures obtained for compounds (1) to (30) are summarized in Table 1.

The starting acidic partners are commercially available or were synthesized by state of the art methods, for example for some of them by reaction between an amine and an anhydride, as exemplified in table 2.

1. Example 1: 2-(2-hydroxyethylcarbamoyl)benzoate;2,3,4,6,7,8,9,10-octahydropyrimido[1,2-a]azepin-1-ium 307.5 g (1.47 mol) of 2-(2-hydroxyethylcarbamoyl)benzoic acid were mixed with 396.7 g ethyleneglycol to give a thick suspension to which were added 223.8 g (1.47 mol) DBU over 48 min while the temperature was maintained between 14° C. and 16° C. 134.6 g additional ethyleneglycol were then added to obtain a thin suspension. After stirring for 3 hours at room temperature, a colorless solution was obtained. $^{13}$C-NMR (CDCl$_3$, 400 MHz, δ ppm): 173.5, 171.5, 166, 137, 136, 129.5, 129, 128, 127, 63 (ethyleneglycol), 61, 54, 48, 42, 38, 32, 29, 26, 24, 19.

2. Example 2: 2-(2-hydroxyethylcarbamoyl)benzoate; 1-ethyl-4-methyl-piperazin-4-ium 5.6 g (50 mmol) DABCO were mixed with 48.2 g of ethyleneglycol to give a white suspension. 10.5 g (50 mmol) of 2-(2-hydroxyethylcarbamoyl)benzoic acid were added under slight cooling to obtain a suspension. The mixture was stirred one hour at room temperature to give a yellowish solution. $^{13}$C-NMR (D$_2$O, 400 MHz, δ ppm): 175.5, 173, 137.5, 134.5, 130.5, 129.5, 129, 128, 62.5 (ethyleneglycol), 60, 44, 42.

3. Example 3: 2-(tert-butylcarbamoyl)benzoate; 2,3,4,6,7,8,9,10-octahydropyrimido[1,2-a]azepin-1-ium 11.1 g (50 mmol) of 2-(tert-butylcarbamoyl)benzoic acid were mixed with 18 g ethyleneglycol, which thick white suspension was cooled down to 15° C. at which temperature it could not be stirred anymore. 37.3 g ethyleneglycol were added. 7.6 g (50 mmol) DBU were added dropwise, followed by 1 g ethyleneglycol. The mixture was stirred for four hours at room temperature to give a clear solution. $^{13}$C-NMR (CDCl$_3$, 400 MHz, δ ppm): 175, 170, 166, 138.5, 135, 129.5, 128, 127.5, 63 (ethyleneglycol), 54, 51.5, 48.5, 38, 32.5, 29.5, 28.5, 26.5, 24, 19.

4. Example 4: 2-(tert-butylcarbamoyl)benzoate; 1-ethyl-4-methyl-piperazin-4-ium 5.6 g (50 mmol) DABCO were mixed with 16.7 g of ethyleneglycol to give a white suspension. 11 g (50 mmol) of 2-(tert-butylcarbamoyl)benzoic acid were added in three portions under slight cooling to obtain a thin white suspension. The mixture was stirred over night at room temperature to give a colorless solution. $^{13}$C-NMR (CDCl$_3$, 400 MHz, δ ppm): 174.5, 170.5, 137, 136.5, 129.5, 129, 128, 127, 63.5 (ethyleneglycol), 51.5, 44.5, 28.5.

5. Example 5: 2-(isopropylcarbamoyl)benzoate; 2,3,4,6,7,8,9,10-octahydropyrimido[1,2-a]azepin-1-ium 10.4 g (50 mmol) of 2-(isopropylcarbamoyl)benzoic acid were mixed with 16 g ethyleneglycol, which white suspension was cooled down to 15° C. 7.6 g (50 mmol) DBU were added dropwise, followed by 2 g ethyleneglycol. The mixture was stirred for three hours to give a clear solution. $^{13}$C-NMR (DMSO, 400 MHz, δ ppm): 173.5, 167.5, 165.5, 142, 132.5, 130, 129, 128.5, 127, 63 (ethyleneglycol), 54, 48, 41, 38, 32, 28.5, 26.5, 23.5, 22.5, 19.5.

6. Example 6: 2-(isopropylcarbamoyl)benzoate; 1-ethyl-4-methyl-piperazin-4-ium 5.6 g (50 mmol) DABCO were mixed with 16.0 g of ethyleneglycol. 10.4 g (50 mmol) of 2-(isopropylcarbamoyl) benzoic acid were added in three portions under slight cooling to obtain a thin white suspension. The mixture was stirred over night at room temperature to give a colorless solution. $^{13}$C-NMR (CDCl$_3$, 400 MHz, δ ppm): 174.5, 170, 137.5, 135.5, 129.5, 129, 128, 127.5, 63.5 (ethyleneglycol), 44.5, 42, 22.

7. Example 7: 2-(propylcarbamoyl)benzoate; 2,3,4,6,7,8,9,10-octahydropyrimido[1,2-a]azepin-1-ium 10.4 g (50 mmol) of 2-(propylcarbamoyl)benzoic acid were mixed with 16 g ethyleneglycol, which white suspension was cooled down to 15° C. 7.6 g (50 mmol) DBU were added dropwise, followed by 2 g ethyleneglycol. The mixture was stirred for two hours to give a clear solution. $^{13}$C-NMR (DMSO, 400 MHz, δ ppm): 173.5, 168.5, 166, 142, 133, 130, 129, 128.5, 127, 63 (ethyleneglycol), 53.5, 48, 41.5, 38, 32, 28.5, 26.5, 24, 22.5, 19.5, 12.

8. Example 8: 2-(propylcarbamoyl)benzoate; 1-ethyl-4-methyl-piperazin-4-ium 5.6 g (50 mmol) DABCO were mixed with 16.0 g of ethyleneglycol. 10.4 g (50 mmol) of 2-(propylcarbamoyl) benzoic acid were added in four portions under slight cooling to obtain a thin white suspension. The mixture was stirred over night at room temperature to give a colorless solution. $^{13}$C-NMR (CDCl$_3$, 400 MHz, δ ppm): 174.5, 171, 138, 135.5, 129.5, 129, 128.5, 127.5, 63.5 (ethyleneglycol), 44.5, 41.5, 22.5, 11.5.

9. Example 9: 4-(tert-butylamino)-4-oxo-butanoate; 2,3,4,6,7,8,9,10-octahydropyrimido[1,2-a]azepin-1-ium 8.7 g (50 mmol) of 4-(tert-butylamino)-4-oxo-butanoic acid were mixed with 14.3 g of ethyleneglycol to give a which suspension to which were added 7.6 g (50 mmol) DBU maintaining the temperature between 14 and 18° C. to give a thin white suspension. 2 g additional ethyleneglycol were then added to obtain a thin suspension. After stirring for 2 hours at room temperature, a colorless solution was obtained. $^{13}$C-NMR (DMSO, 400 MHz, δ ppm): 177, 173, 165, 63 (ethyleneglycol), 53.5, 50, 48, 38, 34.5, 34, 32, 29, 28, 26.5, 24, 19.5.

10. Example 10: 4-(tert-butylamino)-4-oxo-butanoate;1-ethyl-4-methyl-piperazin-4-ium 5.6 g (50 mmol) DABCO were mixed with 35 g ethyleneglycol to give a white suspension. 6 g (50 mmol) of 4-(tert-butylamino)-4-oxo-butanoic acid were added in three portions under slight cooling to obtain a thin white suspension. 7 g ethyleneglycol were added and the mixture was stirred one hour at room temperature to give a colorless solution. $^{13}$C-NMR (DMSO, 400 MHz, δ ppm): 176, 172, 63 (ethyleneglycol), 50, 46, 32, 31.5, 29.

11. Example 11: 4-(isopropylamino)-4-oxo-butanoate; 2,3,4,6,7,8,9,10-octahydropyrimido[1,2-a]azepin-1-ium 8.0 g (50 mmol) of 4-(isopropylamino)-4-oxo-butanoic acid were mixed with 13.6 g of ethyleneglycol to give a white suspension to which were added 7.6 g (50 mmol) DBU maintaining the temperature between 14 and 19° C. to give a thin white suspension. 2 g additional ethyleneglycol were then added to obtain a thin suspension. After stirring for 2 hours at room temperature, a colorless solution was obtained. $^{13}$C-NMR (DMSO, 400 MHz, δ ppm): 177, 172.5, 165.5, 63 (ethyleneglycol), 53.5, 50, 48.5, 38, 34, 33.5, 32, 29, 26.5, 24, 23, 19.5.

12. Example 12: 4-(isopropylamino)-4-oxo-butanoate;1-ethyl-4-methyl-piperazin-4-ium 4.26 g (38 mmol) DABCO were mixed with 8 g ethyleneglycol to give a colorless solution. 6 g (38 mmol) of 4-(isopropylamino)-4-oxo-butanoic acid were added in three portions under slight cooling to obtain a white suspension. 2.3 g ethyleneglycol were added and the mixture was stirred one hour at room temperature to give a colorless solution.

$^{13}$C-NMR (DMSO, 400 MHz, δ ppm): 175.5, 162, 63 (ethyleneglycol), 46, 40.5, 31.5, 31, 23.

13. Example 13: 2-(2-hydroxyethylcarbamoyl)benzoate; 3,4,6,7,8,9-hexahydro-2H-pyrimido[1,2-a]pyrimidin-1-ium 5.0 g (36 mmol) TBD were mixed with 37.6 g ethyleneglycol to give a solution. 7.5 g (36 mmol) of 2-(2-hydroxyethylcarbamoyl)benzoic acid were added in four portions at a temperature maintained between 14 and 19° C. Stirring was continued for 3 hours to give a colorless solution. $^{13}$C-NMR (MeOD, 400 MHz, δ ppm): 174.5, 172, 151, 138.5, 135.5, 129, 128.5, 128, 127, 63 (ethyleneglycol), 60, 46.5, 42.5, 38, 20.5.

14. Example 14: 2-(hydroxycarbamoyl)benzoate;2,3,4,6,7,8,9,10-octahydropyrimido[1,2-a]azepin-1-ium 4.5 g (25 mmol) of 2-(hydroxycarbamoyl)benzoic acid were mixed with 6.34 g of ethyleneglycol to give a yellow suspension to which were added 3.8 g (25 mmol) DBU maintaining the temperature between 14 and 18° C. to give a thin orange suspension. 2 g additional ethyleneglycol were then added to obtain a thin suspension. After stirring for 2 hours at room temperature, the thin suspension was filtered to give a clear orange solution. $^{13}$C-NMR (DMSO, 400 MHz, δ ppm): 177.5, 166, 165, 140.5, 132, 129.5, 129, 128, 63 (ethyleneglycol), 53.5, 48.5, 33, 29, 28, 24.5, 20.

15. Example 15: 2-(hydroxycarbamoyl)benzoate;1-ethyl-4-methyl-piperazin-4-ium 5.1 g (28 mmol) of 2-(hydroxycarbamoyl)benzoic acid were mixed with 8.2 g of ethyleneglycol to give a suspension to which were added 3.1 g (28 mmol) DABCO maintaining the temperature below 22° C. to give a yellow suspension. 8.2 g additional ethyleneglycol were then added to obtain a thin suspension. After stirring for 2 hours at room temperature, the thin suspension was filtered to give a clear yellow solution.

16. Example 16: 4-aminobutanoate; 2,3,4,6,7,8,9,10-octahydropyrimido[1,2-a]azepin-1-ium 5.2 g (50 mmol) of 4-aminobutanoic acid were mixed with 10.8 g of ethyleneglycol to give a white suspension which was cooled down to 13° C. 7.6 g (50 mmol) DBU were added dropwise and 2 g additional ethyleneglycol were then added to give a suspension. 25.5 g additional ethyleneglycol were added and stirring was continued over night to give a colorless solution. $^{13}$C-NMR (DMSO, 400 MHz, δ ppm): 178.5, 165, 63.5 (ethyleneglycol), 53.5, 0.48, 42, 38.5, 36, 32.5, 30, 29, 26.5, 24, 20.

17. Example 17: 4-aminobutanoate;1-ethyl-4-methyl-piperazin-4-ium 4.1 g (40 mmol) of 4-aminobutanoic acid were mixed with 6.6 g of ethyleneglycol to give a white suspension to which were added 4.5 g (40 mmol) DABCO maintaining the temperature below 15° C. 70 g additional ethyleneglycol were then added to obtain a clear solution. $^{13}$C-NMR (D2O, 400 MHz, δ ppm): 181.5, 62.5 (ethyleneglycol), 45, 40, 34.5, 24.

18. Example 18: (Z)-4-(tert-butylamino)-2,3-dimethyl-4-oxo-but-2-enoate; 2,3,4,6,7,8,9,10-octahydropyrimido[1,2-a]azepin-1-ium; 2-methylpropan-2-amine DBU was neutralized by the t-butylammonium salt of the acid.

6.8 g (25 mmol) of (Z)-4-(tert-butylamino)-2,3-dimethyl-4-oxo-but-2-enoate; tert-butylammonium were mixed with 8.6 g of ethyleneglycol to give a white suspension which was cooled down to 17° C. 3.8 g (25 mmol) DBU were added dropwise and 2 g additional ethyleneglycol were then added. Stirring was continued for two hours to give a colorless solution. $^{13}$C-NMR (DMSO, 400 MHz, δ ppm): 176, 170, 165.5, 140.5, 123, 63.5 (ethyleneglycol), 53.5, 50, 48.5, 47.5, 38.5, 32.5, 29, 28.5, 26.5, 24, 19.5, 18.5, 15.

19. Example 19: (Z)-4-(tert-butylamino)-2,3-dimethyl-4-oxo-but-2-enoate; 1-ethyl-4-methyl-piperazin-4-ium; 2-methylpropan-2-amine DABCO was neutralized by the t-butylammonium salt of the acid.

6.1 g (22 mmol) of (Z)-4-(tert-butylamino)-2,3-dimethyl-4-oxo-but-2-enoate; tert-butylammonium were mixed with 6.6 g of ethyleneglycol to give a white suspension which was cooled down to 15° C. 2.5 g (22 mmol) DABCO were added dropwise and 19.1 g additional ethyleneglycol were then added. Stirring was continued for two hours to give a colorless solution. $^{13}$C-NMR (DMSO, 400 MHz, δ ppm): 176.5, 170, 139, 124.5, 63 (ethyleneglycol), 51, 50.5, 47, 39, 38.5, 18, 15.

20. Example 20:2-sulfamoylbenzoate; 2,3,4,6,7,8,9,10-octahydropyrimido[1,2-a]azepin-1-ium 5 g (25 mmol) of 2-sulfamoylbenzoic acid were mixed with 5.6 g of ethyleneglycol to give a white suspension which was cooled down to 13° C. 3.8 g (25 mmol) DBU were added dropwise and 19.7 g additional ethyleneglycol were then added to give a white suspension. 53 g additional ethyleneglycol were then added to give a colorless solution. $^{13}$C-NMR (DMSO, 400 MHz, δ ppm): 171.5, 166, 141, 140.5, 132, 131, 128, 126, 63 (ethyleneglycol), 54, 48.5, 38.5, 32.5, 29.5, 26.5, 24, 19.5.

21. Example 21: 2-sulfamoylbenzoate; 1-ethyl-4-methyl-piperazin-4-ium 6 g (30 mmol) of 2-sulfamoylbenzoic acid were mixed with 7.4 g of ethyleneglycol to give a white suspension which was cooled down to 17° C. 3.4 g (30 mmol) DABCO were added dropwise to give a white suspension. 2 g additional ethyleneglycol were then added. Stirring was continued over night to give a colorless solution. $^{13}$C-NMR (DMSO, 400 MHz, δ ppm): 172, 140.5, 140, 132, 130, 128.5, 126, 63.5 (ethyleneglycol), 44.5.

22. Example 22: 2-(2-amino-2-methyl-propoxy) carbonylbenzoate;2,3,4,6,7,8,9,10-octahydropyrimido[1,2-a]azepin-1-ium 5.9 g (25 mmol) of 2-(2-amino-2-methyl-propoxy)carbonylbenzoic acid were mixed with 8.6 g of ethyleneglycol to give a white suspension which was cooled down to 14° C. 3.8 g (25 mmol) DBU were added dropwise and 2 g additional ethyleneglycol were then added to give a thin white suspension. 21.1 g additional ethyleneglycol were then added and stirring was continued over night to give a colorless solution. $^{13}$C-NMR (DMSO, 400 MHz, δ ppm): 171.5, 166, 141, 140.5, 132, 131, 128, 126, 63 (ethyleneglycol), 54, 48.5, 38.5, 32.5, 29.5, 26.5, 24, 19.5.

23. Example 23: 2-(hydroxymethyl)benzoate; 2,3,4,6,7,8,9,10-octahydropyrimido[1,2-a]azepin-1-ium 3.8 g (25 mmol) of 2-(hydroxymethyl)benzoic acid were mixed with 5.6 g of ethyleneglycol to give a white suspension which was cooled down to 13° C. 3.8 g (25 mmol) DBU were added dropwise and 2 g additional ethyleneglycol were then added to give a thin white suspension. 15.2 additional ethyleneglycol were then added and stirring was continued for three hours to give a colorless solution. $^{13}$C-NMR (DMSO, 400 MHz, δ ppm): 173, 165.5, 141, 139.5, 130.5, 129, 128.5, 127, 64.5, 63 (ethyleneglycol), 54, 48, 38, 32, 28.5, 26.5, 24, 19.

24. Example 24: 2-(hydroxymethyl)benzoate;1-ethyl-4-methyl-piperazin-4-ium 4.9 g (32 mmol) of 2-(hydroxymethyl)benzoic acid were mixed with 6.5 g of ethyleneglycol to give a thick white suspension to which were added 3.6 g (32 mmol) DABCO maintaining the temperature between 15° C. and 17° C. 2 g additional ethyleneglycol. Stirring was continued for 4 hours to obtain a clear solution. $^{13}$C-NMR (DMSO, 400 MHz, δ ppm): 172.5, 142.5, 136.5, 130.5, 130, 128, 127, 64, 63 (ethyleneglycol), 45.

25. Example 25: 4-(propylamino)-4-oxo-butanoate; 2,3,4,6,7,8,9,10-octahydropyrimido[1,2-a]azepin-1-ium 8.0 g (50 mmol) of 4-(propylamino)-4-oxo-butanoic acid were mixed with 13.6 g of ethyleneglycol to give a thick white suspension. 7.6 g (50 mmol) DBU were added dropwise maintaining the temperature between 16 and 17° C. 2 g additional ethyleneglycol were then added to give a thin suspension. Stirring was continued for three hours to give a colorless solution. $^{13}$C-NMR (DMSO, 400 MHz, δ ppm): 177, 173, 165.5, 63.5 (ethyleneglycol), 53.5, 48.5, 40.5, 38, 34, 33.5, 32, 29, 26.5, 24, 23, 19.5, 12.

26. Example 26: 4-(propylamino)-4-oxo-butanoate; 1-ethyl-4-methyl-piperazin-4-ium 5.6 g (50 mmol) DABCO were mixed with 10 g ethyleneglycol to give a colorless solution. 7.96 g (50 mmol) of 4-(propylamino)-4-oxo-butanoic acid were added in three portions under slight cooling to obtain a white suspension. 3.6 g ethyleneglycol were added and the mixture was stirred one hour at room temperature to give a colorless solution. $^{13}$C-NMR (DMSO, 400 MHz, δ ppm): 176, 172, 63 (ethyleneglycol), 45.5, 41, 32, 31.5, 23, 12.

27. Examples 27-30 were Synthesized Using the Same General Method by Adjusting the Ration Between the Starting Acid and the Amine Base

TABLE 1

Structure of compounds (1) to (30)

| No. | Structure |
|---|---|
| 1 | *(structure image)* Molar ratio DBU:Acid 1:1 |
| 2 | *(structure image)* Molar ratio DABCO:Acid 1:1 |
| 3 | *(structure image)* Molar ratio DBU:Acid 1:1 |
| 4 | *(structure image)* Molar ratio DABCO:Acid 1:1 |

TABLE 1-continued

Structure of compounds (1) to (30)

| No. | Structure |
|---|---|
| 5 | [DBU·H+ cation with N-isopropyl phthalamate anion]<br>Molar ratio DBU:Acid<br>1:1 |
| 6 | [DABCO·H+ cation with N-isopropyl phthalamate anion]<br>Molar ratio DABCO:Acid<br>1:1 |
| 7 | [DBU·H+ cation with N-propyl phthalamate anion]<br>Molar ratio DBU:Acid<br>1:1 |
| 8 | [DABCO·H+ cation with N-propyl phthalamate anion]<br>Molar ratio DABCO:Acid<br>1:1 |
| 9 | [DBU·H+ cation with N-tert-butyl succinamate anion]<br>Molar ratio DBU:Acid<br>1:1 |
| 10 | [DABCO·H+ cation with N-tert-butyl succinamate anion]<br>Molar ratio DABCO:Acid<br>1:1 |
| 11 | [DBU·H+ cation with N-isopropyl succinamate anion]<br>Molar ratio DBU:Acid<br>1:1 |
| 12 | [DABCO·H+ cation with N-isopropyl succinamate anion]<br>Molar ratio DABCO:Acid<br>1:1 |

TABLE 1-continued

Structure of compounds (1) to (30)

| No. | Structure |
|---|---|
| 13 | 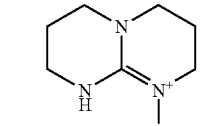<br>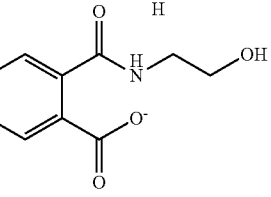<br>Molar ratio TBD:Acid<br>1:1 |
| 14 | 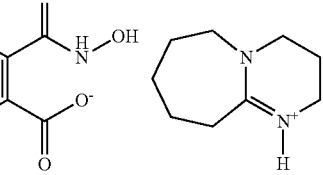<br>Molar ratio DBU:Acid<br>1:1 |
| 15 | <br>Molar ratio DABCO:Acid<br>1:1 |
| 16 | 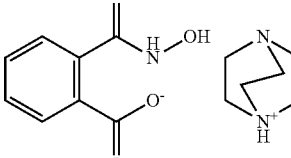<br>Molar ratio DBU:Acid<br>1:1 |
| 17 | <br>Molar ratio DABCO:Acid<br>1:1 |
| 18 | 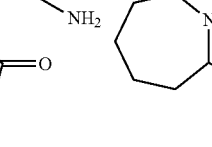<br>Molar ratio DBU:Acid<br>1:1 |
| 19 | <br>Molar ratio DABCO:Acid<br>1:1 |
| 20 | 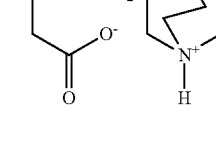<br>Molar ratio DBU:Acid<br>1:1 |
| 21 | <br>Molar ratio DABCO:Acid<br>1:1 |
| 22 | 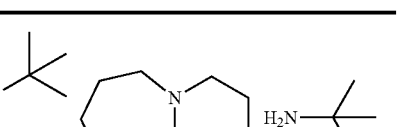<br>Molar ratio DBU:Acid<br>1:1 |
| 23 | 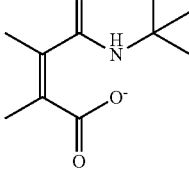<br>Molar ratio DBU:Acid<br>1:1 |

TABLE 1-continued
Structure of compounds (1) to (30)
| No. | Structure |
|---|---|
| 24 | 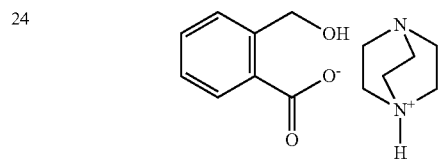 |
Molar ratio DABCO:Acid
1:1
| 25 | 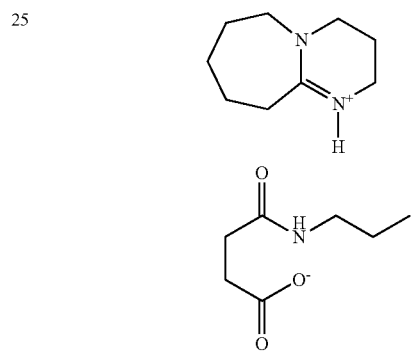 |
Molar ratio DBU:Acid
1:1
| 26 | 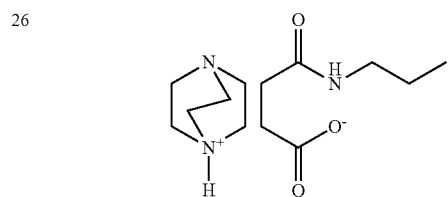 |
Molar ratio DABCO:Acid
1:1
| 27 | 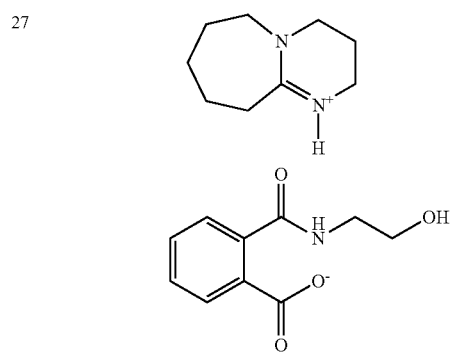 |
Molar ratio DBU:Acid
1:1.25
TABLE 1-continued
Structure of compounds (1) to (30)
| No. | Structure |
|---|---|
| 28 | 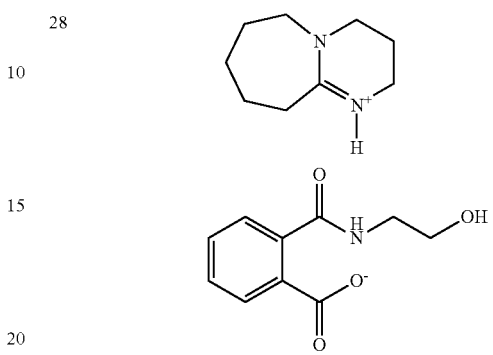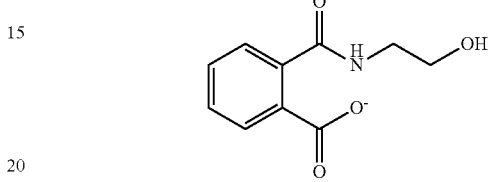 |
Molar ratio DBU:Acid
1:1.5
| 29 | 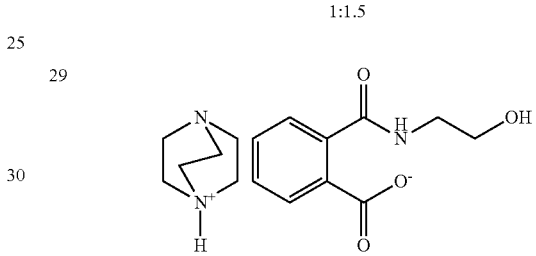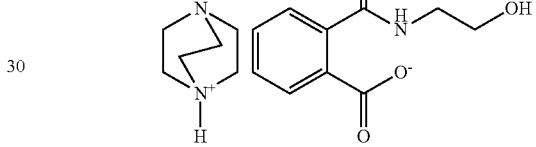 |
Molar ratio DABCO:Acid
1:1.25
| 30 | 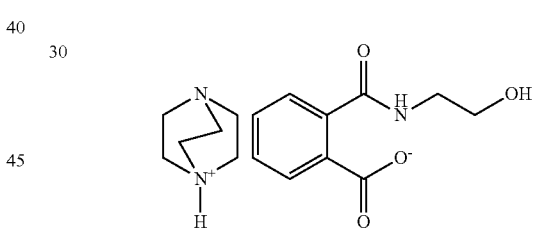 |
Molar ratio DABCO:Acid
1:1.5
| 31 | 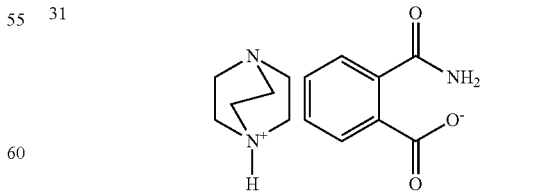 |
Molar ratio DABCO:Acid
1:1

TABLE 2

| starting acidic partners | | |
|---|---|---|
| Acidic partner | Number of the corresponding salt(s) | reference |
| 2-(tert-butylcarbamoyl)benzoic acid | 3, 4 | Kaicharla, Trinadh; Thangaraj, Manikandan; Biju, Akkattu T. *Organic Letters* 2014, 16, 1728-1731. |
| 2-(isopropylcarbamoyl)benzoic acid | 5, 6 | Verbicky, John W., Jr.; Williams, Louella *Journal of Organic Chemistry* 1981, 46, 175-7. |
| 2-(propylcarbamoyl)benzoic acid | 7, 8 | Yasuda, Naohiko; Nakamura, Asao; Tsuboi, Masamichi *Journal of Heterocyclic Chemistry* 1987, 24, 303-7 |
| 4-(tert-butylamino)-4-oxo-butanoic acid | 9, 10 | Zhang, Fu-chen; Gong, Sheng-chen; Chen, Qi-fan *Liaodong Xueyuan Xuebao, Ziran Kexueban* 2010, 17, 1-4. |
| 4-(isopropylamino)-4-oxo-butanoic acid | 11, 12 | Valla, Alain; Cartier, Dominique; Zentz, Frederic; Labia, Roger *Synthetic Communications* 2006, 36, 3591-3597. |
| 2-(hydroxycarbamoyl)benzoic acid | 14, 15 | Wang, Wen-Hua; Liu, Wei-Sheng; Wang, Ya-Wen; Li, Yang; Zheng, Li-Fang; Wang, Da-Qi *Journal of Inorganic Biochemistry* 2007, 101, 297-304. |

TABLE 2-continued starting acidic partners

| Acidic partner | Number of the corresponding salt(s) | reference |
|---|---|---|
| 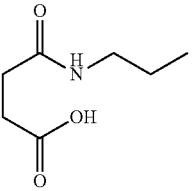<br>4-oxo-4-(propylamino)butanoic acid | 25, 26 | Tanaka, Kazuo; Ishiguro, Fumiyasu; Chujo, Yoshiki *Journal of the American Chemical Society* 2010, 132, 17649-17651. |
| 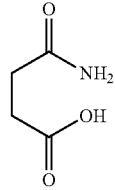<br>4-amino-4-oxo-butanoic acid | 31 | Commercially available |

II. Preparation of Polyurethanes
1. Formulation

| Polyol | wt. % |
|---|---|
| Polyol A | 32 |
| Polyol B | 30 |
| Polyol C | 35 |
| Additive 1 | 2.9 |
| Additive 2 | 0.1 |
| Catalyst (active species) | 0.05 |

| Isocyanate | wt. % |
|---|---|
| Iso A | 40 |
| Iso B | 60 |
| MV | 100:98 |

Polyol A: Polyetherpolyol with an average OH value of 248 mg KOH/g, a functionality of 2.0 and a propylene oxide content, respect to the polymer weight, of approx. 83 wt. %

Polyol B: Isopol 1200-3600 of the company ISO-ELEKTRA Elektrochemische Fabrik GmbH Polyol C: Polyetherpolyol with an average OH value of 490 mg KOH/g, a functionality of 4.3 and a propylene oxide content, respect to the polymer weight, of approx. 67 wt. %

Additive 1: Zeolite-Paste 3A from the company ISO-ELEKTRA Elektrochemische Fabrik GmbH Additive 2: Xiameter ACP-1000 Antifoam compound from the company Dow Corning Corporation Iso A: Poly(methylen-diphenyl-diisocyanate) with a NCO content of 31.5 wt. % and an average functionality of 2.7

Iso B: Methylene-diphenyl-diisocyanat with a NCO content of 33.5 Gew.-% and an average functionality of 2, with an isomeric 4,4' content of 49 wt. %

2. Preparation of the Novel Catalyst.

In a typical experiment, 50 wt. % ethylene glycol solution of the different salts were prepared. The corresponding amounts of acid, base and solvent were added and shortly heated in a microwave oven (900 Watts) for 20 sec. After that the mixture was vigorously stirred for 10 sec to obtain a homogeneous solution.

3. Catalyst

The amount specified in the formulation corresponds to the concentration of catalytic species.

Cat. Ref. 1: 1,8-diazabicyclo-5,4,0-undecen-7 (DBU) from BASF AG

Cat. Ref. 2: Polycat® SA1-10 from Air Products

Cat. Ref. 3: 50 wt. % ethylene glycol solution of 1 eq. of phthalamic acid (Aldrich) and DBU from BASF AG Cat. Ref. 4: structure from JP2014055114A 20140327

3.1 For the preparation of Cat. Ref. 4, the acidic component was prepared according to Jha, Amitabh; Chou, Ting-Yi; Al Jaroudi, Zainab; Ellis, Bobby D.; Cameron, T. Stanley, Beilstein Journal of Organic Chemistry, 2014, 10, 848-857.

The acid was mixed with ethyleneglycol to give a thick suspension to which DBU was added while the temperature was maintained between 14° C. and 16° C. After stirring for 3 hours at room temperature, a colorless solution was obtained.

4. Curing with the DSC

The polyol component was mixed using a speed mixer for 5 min under vacuum conditions. Then, the isocyanates component was added and the components were mixed again with a speed mixer under vacuum for additional 2 min. Approximately 10 mg was weighted into a DSC Al-pan. The reactive mixture was then heated from 30° C. to 250° C. at 20 K/min. An example can be appreciated in FIG. 1. The curing reaction was recorded. The onset, peak and offset temperatures were extracted from the curve, the results can be appreciated in Table 3. They were calculated by estimating the area under the curve. The temperatures at 10%, 50% and 95% area were considered as the onset, peak and offset temperatures, respectively.

The cured resin was cooled down (30° C.) and re-heated (150° C.). The glass transition of the cured resin was approx. 80° C. in all the cases.

The latency of the DBU-carboxylate can be measured as the shift of the temperature peak during the curing reaction. A good thermolatent catalyst would be one that shift the onset of the temperature of the curing reaction by keeping, at least, the same offset temperature as the reference (DBU).

From the results can be observed that the DBU carboxylate prepared with succinamic acid has the better latency (shift of temperature at 10% curing) and lower end-curing temperature (temperature at 95% degree of curing). By using the DBU carboxylate prepared with 4-oxo-4-(propylamino) butanoic acid, a minimum shift in the 10% temperature is observed by comparable end-curing temperature to polycat SA1-10.

The thermolatency of the different DBU carboxylates can be also evaluated by varying the ratio DBU:acid ratio. Table 4 summarizes the results. Surprisingly, in the case of the 4-oxo-4-(propylamino)butanoic acid the increase in its concentrations, related to DBU, shifted the onset of the curing reaction and shortens the offset temperature.

TABLE 3

Comparison uncatalyzed with catalyzed system. Molar ratio DBU to acid 1:1

| | | From the area | | |
|---|---|---|---|---|
| ID | Catalyst | 10% (° C.) | 50% (° C.) | 95% (° C.) |
| 1 | | 93 | 138 | 207 |
| 2 | Cat. Ref. 1 | 78 | 102 | 132 |
| 3 | Cat. Ref. 2 | 77 | 101 | 130 |
| 4 | Cat. Ref. 3 | 82 | 107 | 137 |
| 5 | Cat. Ref. 4 | 78 | 103 | 134 |
| | 4-methoxyphthalanilic acid:DBU 1:1 | | | |
| 6 | Succinamic acid:DBU 1:1 | 80 | 104 | 130 |
| 7 | 4-oxo-4-(propylamino)butanoic acid:DBU 1:1 (25) | 79 | 103 | 132 |
| 8 | 2-(propyl carbomoyl)benzoic acid:DBU 1:1 (1) | 80 | 104 | 134 |
| 9 | 2-(hydroxymethyl)benzoic acid:DBU 1:1 (23) | 81 | 104 | 132 |
| 10 | 7 | 80 | 111 | 143 |
| 11 | 4-methoxysuccinanilic acid:DBU 1:1 | 79 | 101 | 127 |

TABLE 4

Comparison different DBU molar ratio. Variation of Molar ratio between DBU and acid

| | | From the area | | |
|---|---|---|---|---|
| ID | Catalyst | 10% (° C.) | 50% (° C.) | 95% (° C.) |
| 1 | 4-oxo-4-(propylamino)butanoic acid:DBU 1:1 (25) | 79 | 103 | 132 |
| 3 | 4-oxo-4-(propylamino)butanoic acid:DBU 1.5:1 | 80 | 102 | 129 |
| 4 | 4-oxo-4-(propylamino)butanoic acid:DBU 2:1 | 81 | 102 | 129 |
| 5 | 4-oxo-4-(propylamino)butanoic acid:DBU 3:1 | 80 | 105 | 132 |
| 6 | 4-oxo-4-(propylamino)butanoic acid:DBU 4:1 | 81 | 104 | 128 |
| 7 | 4-oxo-4-(propylamino)butanoic acid:DBU 10:1 | 81 | 117 | 157 |
| 8 | 2-(propylcarbomoyl)benzoic acid:DBU 1:1 (1) | 80 | 104 | 134 |
| 9 | 2-(propylcarbomoyl)benzoic acid:DBU 1.5:1 | 81 | 107 | 138 |
| 10 | Cat. Ref. 3 | 82 | 107 | 137 |
| 11 | Phthalamic acid:DBU 1.5:1 | 81 | 107 | 140 |
| 12 | 2-(hydroxymethyl)benzoic acid:DBU 1:1 (23) | 81 | 104 | 131 |
| 13 | 2-(hydroxymethyl)benzoic acid:DBU 2:1 | 81 | 112 | 139 |
| 14 | 2-(hydroxymethyl)benzoic acid:DBU 3:1 | 81 | 115 | 141 |
| 15 | Succinamic acid:DBU 1:1 | 80 | 101 | 125 |
| 16 | Succinamic acid:DBU 1:1 | 81 | 105 | 135 |
| 17 | Succinamic acid:DBU 2:1 | 80 | 106 | 136 |
| 18 | Succinamic acid:DBU 4:1 | 79 | 105 | 134 |
| 19 | Succinamic acid:DBU 10:1 | 74 | 112 | 142 |

5. Production of Plates Via Reaction Transfer Molding

Plates were produced via reaction transfer molding.

A commercial RTM formulation, named BASF Ellastolit R8819/104 LT was tested. 14 cm×12 cm×2 mm plates were prepared with/without Toray T700 carbon fiber fabrics at 90° C. and 110° C. (mold temperature). Without carbon fibers it can be appreciated that the plates catalyzed with ID1 (Table 4) are more transparent than the original Ellastolit formulation. In the case of the fiber reinforced plates, the addition of the catalyst ID 1 (Table 4) reduced the de-molding time at 90° C. from 3 to 2 min and at 110° C. from higher than to 2 to 2 min. The use of catalyst ID 1 (Table 4) reduces the de-molding time of an approx. 30%. Most translucent PU composite parts are an advantage for the monitoring of defect (e.g. fiber orientation, hot spots, enclosed air, etc.) during production.

The invention claimed is:

1. A process for preparing a polyurethane comprising reacting at least one polyisocyanate with a polyol composition, wherein the polyol composition comprises at least one polyol and a catalyst composition;

wherein the catalyst composition comprises at least one compound (C) selected from the group consisting of compounds of the general formula (Ia) and compounds of the general formula (Ib)

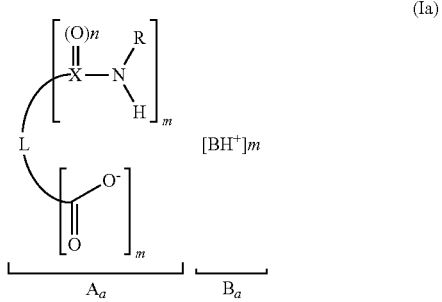

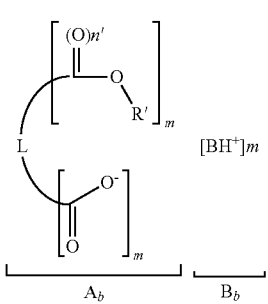

(Ib)

wherein
n is 0 or 1 when X is a carbon atom,
n is 2 when X is a sulfur atom,
n' is 0 or 1,
m is an integer from 1 to 6,
R is H, OH, substituted or unsubstituted, linear or branched $C_1$-$C_{18}$ alkyl, $C_5$-$C_7$ cycloalkyl which can be substituted by OH, $OR^1$ or $NR^2R^3$, and which may be interrupted by one or more —O—, —S— or —$NR^4$—;
R' is linear or branched $C_1$-$C_5$ alkyl substituted by $NHR^2$,
B is a nitrogen containing organic base,
L is $C_1$-$C_8$ substituted or unsubstituted alkylene chain, or a substituted or unsubstituted $C_6$ cycloalkylene chain, or substituted or unsubstituted $C_9$-$C_{11}$ polycyclic chain, or a substituted or unsubstituted double bond, which can be interrupted by O, S, $NR^4$, or a substituted or unsubstituted $C_3$ to $C_4$ alkenylene chain, or a substituted or unsubstituted benzene ring, or substituted or unsubstituted naphthalene ring,
$R^1$ is H, $C_1$-$C_{18}$ alkyl,
$R^2$ and $R^3$, independently are hydrogen, unsubstituted or substituted $C_1$-$C_{18}$ alkyl or phenyl; or $R^2$ and $R^3$ together with the nitrogen atom to which they are bonded form a 5 or 6 membered-ring which may contain a further heteroatom,
$R^4$ is H, unsubstituted or substituted $C_1$-$C_{18}$ alkyl,
the ratio between $A_a$ and $B_a$ or between $A_b$ and $B_b$ ranges from 0.5:1 to 10:1.

2. The process according to claim 1, wherein the compound (C) is selected from the group consisting of compounds of the general formula (Ia) and compounds of the general formula (Ib)

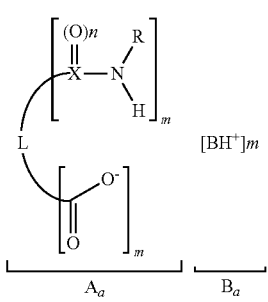

(Ia)

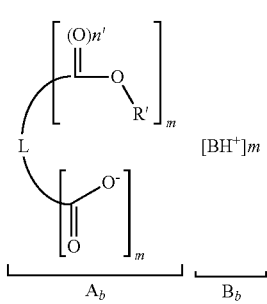

(Ib)

wherein
n is 1 when X is a carbon atom,
n is 2 when X is a sulfur atom,
n' is 0 or 1,
m is 1 or 2,
R is H, OH, linear or branched $C_1$-$C_{18}$ alkyl, $C_5$-$C_7$ cycloalkyl which may be interrupted by one or more —O—, —S— or —$NR^4$—;
R' is linear or branched $C_1$-$C_5$ alkyl substituted by $NHR^2$,
B is substituted or unsubstituted 1,8-Diazabicyclo[5.4.0]undec-7-en (DBU), 1,5-Diazabicyclo[4.3.0]non-5-ene (DBN), Triazabycyclodecene (TBD), 1,4-Diazabicyclo[2.2.2]octan (DABCO), 1,1,3,3-tetramethylguanidine (TMG), or substituted or unsubstituted tertiary aliphatic amines,
L is $C_1$-$C_8$ substituted or unsubstituted alkylene chain, or a substituted or unsubstituted double bond, or a substituted or unsubstituted $C_3$ to $C_4$ alkenylene chain, or has the formula:

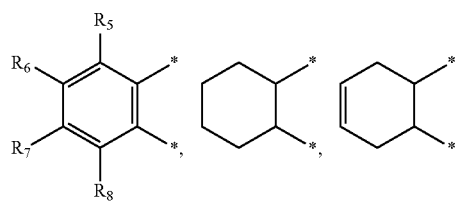

when m is 1 or has the formula:

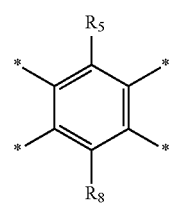

when m is 2
$R^5$, $R^6$, $R^7$, $R^8$ independently from each other are hydrogen, unsubstituted or substituted $C_1$-$C_{28}$ alkyl, $C_2$-$C_{28}$ alkenyl, $C_7$-$C_9$ aralkyl, $C_3$-$C_{20}$ heteroalkyl, $C_5$-$C_{16}$ heteroaralkyl, phenyl or naphthyl, $OR^1$, $NR^2R^3$, or halogen,
or
$R^5$ and $R^6$, $R^6$ and $R^7$ or $R^7$ and $R^8$ are linked together to form 1, 2, 3 or 4 carbocyclic or heterocyclic rings, which may be uninterrupted or interrupted by one or more —O—, —S— or —NR⁴—;

$R^1$ is H, $C_1$-$C_{18}$ alkyl, $R^2$, $R^3$, independently are hydrogen, unsubstituted or substituted $C_1$-$C_{18}$ alkyl or phenyl; or $R^2$ and $R^3$ together with the nitrogen atom to which they are bonded form a 5 or 6 membered-ring which may contain a further heteroatom, $R^4$ is H, unsubstituted or substituted $C_1$-$C_{18}$ alkyl, the ratio between $A_a$ and $B_a$ or between $A_b$ and $B_b$ ranges from 1:1 to 4:1.

3. The process according to claim 1, wherein the compound (C) is selected from the group consisting of compounds of the general formula (I'a) and compounds of the general formula (I'b)

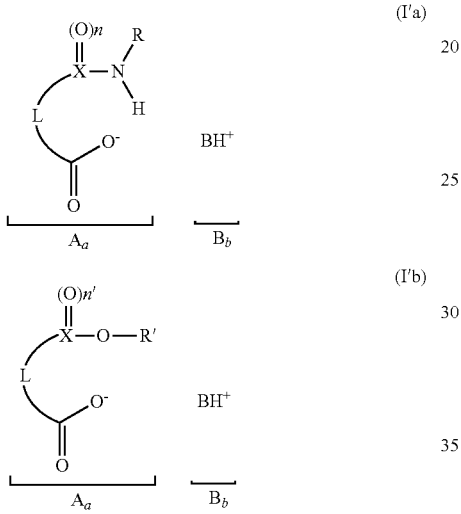

wherein
n is 1 when X is a carbon atom,
n is 2 when X is a sulfur atom,
n' is 0 or 1,
R is H, linear or branched $C_1$-$C_{18}$ alkyl or $C_5$-$C_7$ cycloalkyl,
R' is linear or branched $C_1$-$C_5$ alkyl substituted by $NH_2$ or $NH(C_1$-$C_{18}$ alkyl),
B is 1,8-Diazabicyclo[5.4.0]undec-7-en (DBU), 1,5-Diazabicyclo[4.3.0]non-5-ene (DBN), Triazabycyclodecene (TBD), 1,4-Diazabicyclo[2.2.2]octan (DABCO), 1,1,3,3-tetramethylguanidine (TMG), or tertiary aliphatic amines,
L is $C_1$-$C_8$ substituted or unsubstituted alkylene chain, or a substituted or unsubstituted double bond, or a substituted or unsubstituted $C_3$ to $C_4$ alkenylene chain, or has the formula:

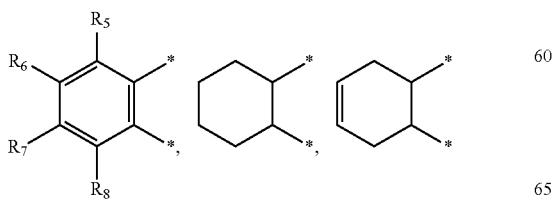

$R^5$, $R^6$, $R^7$, $R^8$ independently from each other are hydrogen, unsubstituted or substituted $C_1$-$C_{28}$ alkyl, $C_2$-$C_{28}$ alkenyl, $C_7$-$C_9$ aralkyl, $C_3$-$C_{20}$ heteroalkyl, $C_5$-$C_{16}$ heteroaralkyl, phenyl or naphthyl, $OR^1$, $NR^2R^3$, or halogen, or $R^5$ and $R^6$, $R^6$ and $R^7$ or $R^7$ and $R^8$ are linked together to form 1, 2, 3 or 4 carbocyclic or heterocyclic rings, which may be uninterrupted or interrupted by one or more —O—, —S— or —NR⁴—;

$R^1$ is H, $C_1$-$C_{18}$ alkyl, $R^2$, $R^3$, independently are hydrogen, unsubstituted or substituted $C_1$-$C_{18}$ alkyl or phenyl; or $R^2$ and $R^3$ together with the nitrogen atom to which they are bonded form a 5 or 6 membered-ring which may contain a further heteroatom, $R^4$ is H, unsubstituted or substituted $C_1$-$C_{18}$ alkyl, the ratio between $A_a$ and $B_a$ or between $A_b$ and $B_b$ ranges from 1:1 to 4:1.

4. The process according to claim 1, wherein the compound (C) is selected from the group consisting of compounds of the general formula (I"a) and compounds of the general formula (I"b)

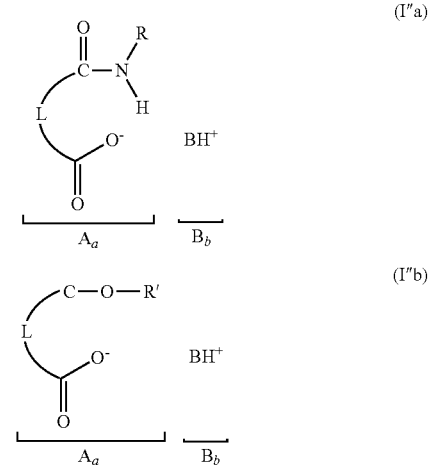

wherein
R is H, linear or branched $C_1$-$C_{18}$ alkyl or $C_5$-$C_7$ cycloalkyl,
R' is linear or branched $C_1$-$C_5$ alkyl substituted by $NH_2$ or $NH(C_1$-$C_{18}$ alkyl),
B is 1,8-Diazabicyclo[5.4.0]undec-7-en (DBU), 1,5-Diazabicyclo[4.3.0]non-5-ene (DBN), Triazabycyclodecene (TBD), 1,4-Diazabicyclo[2.2.2]octan (DABCO), 1,1,3,3-tetramethylguanidine (TMG), or tertiary aliphatic amines,
L is a $C_1$ to $C_8$ substituted or unsubstituted alkylene chain, or has the formula:

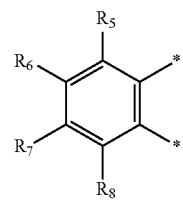

$R^5$, $R^6$, $R^7$, $R^8$ independently from each other are hydrogen, unsubstituted or substituted $C_1$-$C_{28}$ alkyl, $C_2$-$C_{28}$ alkenyl, $C_7$-$C_9$ aralkyl, $C_3$-$C_{20}$ heteroalkyl, $C_5$-$C_{16}$ heteroaralkyl, phenyl or naphthyl, $OR^1$, $NR^2R^3$, or halogen, or $R^5$ and $R^6$, $R^6$ and $R^7$ or $R^7$ and $R^8$ are linked together to form 1, 2, 3 or 4 carbocyclic or heterocyclic rings, which may be uninterrupted or interrupted by one or more —O—, —S— or —$NR^4$—;

$R^1$ is H, $C_1$-$C_{18}$ alkyl, $R^2$, $R^3$, independently are hydrogen, unsubstituted or substituted $C_1$-$C_{18}$ alkyl or phenyl; or $R^2$ and $R^3$ together with the nitrogen atom to which they are bonded form a 5 or 6 membered-ring which may contain a further heteroatom, $R^4$ is H, unsubstituted or substituted $C_1$-$C_{18}$ alkyl, the ratio between $A_a$ and $B_a$ or between $A_b$ and $B_b$ ranges from 1:1 to 4:1.

5. The process according to claim 1, wherein the compound (C) is selected from the group consisting of compounds of the general formula (I″a) and compounds of the general formula (I″b)

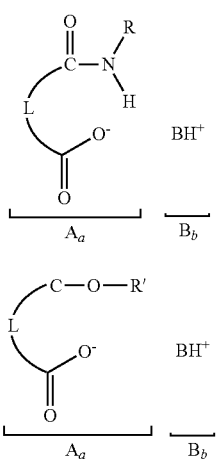

wherein

R is H, linear or branched $C_1$-$C_{18}$ alkyl or $C_5$-$C_7$ cycloalkyl,

R' is linear or branched $C_1$-$C_5$ alkyl substituted by $NH_2$ or $NH(C_1$-$C_{18}$ alkyl), B is 1,8-Diazabicyclo[5.4.0]undec-7-en (DBU), L is a $C_1$ to $C_8$ substituted or unsubstituted alkylene chain, or has the formula:

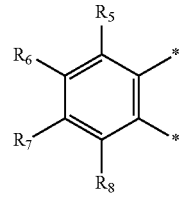

$R^5$, $R^6$, $R^7$, $R^8$ independently from each other are hydrogen, unsubstituted or substituted $C_1$-$C_{28}$ alkyl, $C_2$-$C_{28}$ alkenyl, $C_7$-$C_9$ aralkyl, $C_3$-$C_{20}$ heteroalkyl, $C_5$-$C_{16}$ heteroaralkyl, phenyl or naphthyl, $OR^1$, $NR^2R^3$, or halogen, or $R^5$ and $R^6$, $R^6$ and $R^7$ or $R^7$ and $R^8$ are linked together to form 1, 2, 3 or 4 carbocyclic or heterocyclic rings, which may be uninterrupted or interrupted by one or more —O—, —S— or —$NR^4$—;

$R^1$ is H, $C_1$-$C_{16}$ alkyl, $R^2$, $R^3$, independently are hydrogen, unsubstituted or substituted $C_1$-$C_{18}$ alkyl or phenyl; or $R^2$ and $R^3$ together with the nitrogen atom to which they are bonded form a 5 or 6 membered-ring which may contain a further heteroatom, $R^4$ is H, unsubstituted or substituted $C_1$-$C_{18}$ alkyl, the ratio between $A_a$ and $B_a$ or between $A_b$ and $B_b$ ranges from 1:1 to 4:1.

6. The process according to claim 1, wherein the catalyst composition comprises at least one further catalyst.

7. The process according to claim 1, wherein the at least one polyisocyanate is selected from MDI, polymeric MDI, and TDI, and also derivatives thereof or prepolymers of these polyisocyanates.

* * * * *